US012702689B2

(12) United States Patent
Zhou et al.

(10) Patent No.: US 12,702,689 B2
(45) Date of Patent: Aug. 11, 2026

(54) ANTI-INFLAMMATORY COMPOSITIONS, AND USES THEREOF

(71) Applicants: P.L. THOMAS & CO., INC., Morristown, NJ (US); UNIVERSITY OF CONNECTICUT, Farmington, CT (US); LAILA NUTRACEUTICALS, Vijayawada (IN)

(72) Inventors: Yanjiao Zhou, Farmington, CT (US); Seth Flowerman, Morristown, NJ (US); Ganga Raju Gokaraju, Vijayawada (IN); Rama Raju Gokaraju, Vijayawada (IN)

(73) Assignees: P.L. Thomas & Co., Inc., Morristown, NJ (US); University of Connecticut, Farmington, CT (US); Lalla Nutraceuticals, Vijayawada (IN)

( * ) Notice: Subject to any disclaimer, the term of this patent is extended or adjusted under 35 U.S.C. 154(b) by 324 days.

(21) Appl. No.: 18/453,497

(22) Filed: Aug. 22, 2023

(65) Prior Publication Data

US 2024/0058409 A1 Feb. 22, 2024

Related U.S. Application Data

(60) Provisional application No. 63/399,775, filed on Aug. 22, 2022.

(51) Int. Cl.

| | |
|---|---|
| ***A61K 39/02*** | (2006.01) |
| ***A61K 31/22*** | (2006.01) |
| ***A61K 35/745*** | (2015.01) |
| ***A61K 36/324*** | (2006.01) |
| ***A61P 11/06*** | (2006.01) |
| ***A61P 37/08*** | (2006.01) |

(52) U.S. Cl.

CPC ............ *A61K 36/324* (2013.01); *A61K 31/22* (2013.01); *A61K 35/745* (2013.01); *A61P 11/06* (2018.01); *A61P 37/08* (2018.01)

(58) Field of Classification Search

CPC combination set(s) only.
See application file for complete search history.

(56) References Cited

FOREIGN PATENT DOCUMENTS

IT 201800005002 * 11/2019

OTHER PUBLICATIONS

Jaros et al (Molecules. Jun. 13, 2022. 27(3795): 1-14).*
Salman et al (Indian J. of Forensic Med. & Toxicology, Jul.-Sep. 2021, 15(3): 3371-3376).*
Liu et al (Int J Clin Exp Pathol. Jan. 1, 2015;8(1):236-243.).*
Suther et al (Nutrients. Feb. 15, 2022. 14(814): 1-13).*
Frati, F. et al. The role of the microbiome in asthma: The gut-lung axis. Int. J. Mol. Sci. 20, 1-12 (2019).
Roy, N. K. et al. An Update on Pharmacological Potential of Boswellic Acids against Chronic Diseases. Int. J. Mol. Sci. 2019, vol. 20, p. 4101 20, 4101 (2019).
Beigelman, A. et al. Azithromycin attenuates airway inflammation in a noninfectious mouse model of allergic asthma. Chest 136, 498-506 (2009).
Smith-Brown, P., et al., Dairy and plant based food intakes are associated with altered faecal microbiota in 2 to 3 year old Australian children. Sci. Reports 2016 61 6, 1-8 (2016).
Ferrara, T., et al., Functional study on Boswellia phytosome as complementary intervention in asthmatic patients. Eur. Rev. Med. Pharmacol. Sci. 19, 3757-3762 (2015).
Yugandhar, P., et al., A novel herbal composition containing extracts of Boswellia serrata gum resin and Aegle marmelos fruit alleviates symptoms of asthma in a placebo controlled double-blind clinical study. Phyther. Res. 32, 140-150 (2018).

* cited by examiner

*Primary Examiner* — Jennifer E Graser
(74) *Attorney, Agent, or Firm* — Kramer & Amado, P.C.

(57) ABSTRACT

A gut microbiome may be modulated in a patient in need thereof, by administering a composition comprising 3-O-acetyl-11-keto-b-boswellic acid (AKBA) or an extract of *Boswellia serrata* comprising from 30% to 90% AKBA to the patient; wherein the composition is administered at a dose sufficient to change the ratio between a first organism in the gut microbiome and a second organism in the gut microbiome, compared to a subject not treated with the composition. Modulation of the gut microbiome with AKBA may be used to treat allergic pulmonary inflammation in the patient. Modulation of the gut microbiome with AKBA may be used to maintain diversity and/or increase a percentage of *Bifidobacterium pseudolongum* in the gut microbiome of the patient. The composition may further comprise a lyophilized probiotic bacteria. The composition may be administered in combination with a second composition comprising a lyophilized probiotic bacteria.

11 Claims, 17 Drawing Sheets

| Group | Baseline (g) | Endpoint (g) | Overall % change |
|---|---|---|---|
| OVA control | 19.93±1.02 [a] | 21.59±1.85 [a] | +8.36±6.18% [a] |
| OVA + AKBA | 19.83±1.23 [a] | 19.37±1.20 [b] | -2.32±4.19% [b] |
| Naive | 19.35±0.94 [a] | 20.33±1.12 [a] | +5.04±0.71% [a] |

| Group | Baseline (g) | Endpoint (g) | Overall % change |
|---|---|---|---|
| OVA control | 20.48±0.95 [a] | 22.04±1.54 [a] | +7.47±4.64% [a] |
| OVA + *B. pseudolongum* | 20.72±1.69 [a] | 21.06±1.26 [a] | +1.46±4.07% [b] |
| Naive | 20.02±1.21 [a] | 21.68±1.46 [a] | +8.25±1.50% [a] |

ANTI-INFLAMMATORY COMPOSITIONS, AND USES THEREOF

CROSS-REFERENCE TO RELATED APPLICATIONS

This application claims the benefit of U.S. Provisional Application No. 63/399,775, filed on Aug. 22, 2023, the entire disclosure of which is incorporated herein by reference.

FIELD OF THE DISCLOSURE

The subject disclosure relates to compositions and methods for modulation of the gut microbiome for the treatment or prevention of a disease or disorder wherein the disease or disorder is a disease or disorder associated with inflammation (for example, asthma or allergic diseases) that are effective and have less side effect. The subject disclosure also relates to compositions and methods for inducing or supporting weight loss, or preventing or reducing weight gain in a subject.

BACKGROUND

Allergy is defined as an abnormal immune reaction to the repeated exposure of certain antigens. Continuous exposure of the airways to inhalant antigens, in sensitized individuals, may trigger allergic asthma. Allergic asthma is the most common phenotype of asthma, especially in children. The disease is characterized by inflammation and remodeling of the bronchial tubes, causing airway obstruction and over production of mucus. This leads to the clinical manifestations of asthma, including repeated episodes of wheezing, shortness of breath, and cough. Severe exacerbations may be life threatening and are associated with progressive loss of lung function. Asthma exacerbations have high impact on children, their families, the health care system, and may lead to subsequent decline in lung function. As asthma is associated with significant morbidity and mortality, there is a need to expend therapeutic options.

SUMMARY

In light of the present need for improved treatment of respiratory allergies and/or inflammation, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various embodiments relate to methods of modulating a gut microbiome in a patient in need thereof, by:

administering a composition comprising 3-O-acetyl-11-keto-b-boswellic acid (AKBA) or an extract of *Boswellia serrata* comprising from 30% to 90% AKBA, from 40% to 85% AKBA, from 50% to 80% AKBA, from 60% to 88% AKBA, or from 70% to 85% AKBA, to the patient;

wherein the composition is administered at a dose sufficient to change the ratio between a first organism in the gut microbiome and a second organism in the gut microbiome, compared to a subject not treated with the composition.

In the method of modulating a gut microbiome, the first organism may be a member of the phylum Actinobacteria, the second organism may be a member of the phylum Firmicutes; and the ratio between the first organism and the second organism may be increased by administration of the composition. The first organism may be a member of a genus selected from the group consisting of *Bifidobacterium*, Lactiplantibacillus, Lacticaseibacillus, and *Turicibacter*; the second organism is a member of a genus selected from the group consisting of *Hyphomicrobium, Solirubrobacter*, and *Steroidobacter*; and the ratio between the first organism and the second organism may be increased by administration of the composition. The first organism may be a member of a *Bifidobacterium* genus, such as *Bifidobacterium pseudolongum.*

In various embodiments, methods of modulating a gut microbiome in a patient in need thereof include:

administering a composition containing 3-O-acetyl-11-keto-b-boswellic acid (AKBA) or an extract of *Boswellia serrata* comprising from 30% to 90% AKBA, from 40% to 85% AKBA, from 50% to 80% AKBA, from 60% to 88% AKBA, or from 70% to 85% AKBA, to the patient;

wherein the composition further contains a live or lyophilized probiotic bacteria;

wherein the composition is administered at a dose sufficient to change the ratio between a first organism in the gut microbiome and a second organism in the gut microbiome, compared to a subject not treated with the composition. The live or lyophilized probiotic bacteria may be *Bifidobacterium pseudolongum.*

In various embodiments, methods of modulating a gut microbiome in a patient in need thereof include:

administering a first composition including 3-O-acetyl-11-keto-b-boswellic acid (AKBA) or an extract of *Boswellia serrata* comprising from 30% to 90% AKBA, from 40% to 85% AKBA, from 50% to 80% AKBA, from 60% to 88% AKBA, or from 70% to 85% AKBA, to the patient; and administering a second composition including a live or lyophilized probiotic bacteria to the patient;

wherein the first and second compositions are administered at a dose sufficient to change the ratio between a first organism in the gut microbiome and a second organism in the gut microbiome, compared to a subject not treated with the composition.

Various embodiments relate to methods of treating allergic pulmonary inflammation in a patient in need thereof, by:

administering a composition comprising AKBA or an extract of *Boswellia serrata* comprising from 30% to 90% AKBA, from 40% to 85% AKBA, from 50% to 80% AKBA, from 60% to 88% AKBA, or from 70% to 85% AKBA, to the patient;

wherein the composition is administered at a dose sufficient to change the ratio between a first organism in the gut microbiome and a second organism in the gut microbiome, compared to a subject not treated with the composition. The allergic pulmonary inflammation may be allergic asthma.

In the methods of treating allergic pulmonary inflammation, the first organism may be a member of the phylum Actinobacteria, the second organism may be a member of the phylum Firmicutes; and the ratio between the first organism and the second organism may be increased by administration of the composition. The first organism may be a member of a genus selected from the group consisting of *Bifidobacterium*, Lactiplantibacillus, Lacticaseibacillus, and *Turicibacter*; the second organism is a member of a genus selected from the group consisting of *Hyphomicrobium, Solirubrobacter*, and *Steroidobacter*; and the ratio between the first organism and the second organism may be increased by administration of the composition. The first organism may be a member of a *Bifidobacterium* genus, such as *Bifidobacterium pseudolongum.*

In various embodiments, methods of treating allergic pulmonary inflammation in a patient in need thereof include:

administering a composition containing 3-O-acetyl-11-keto-b-boswellic acid (AKBA) or an extract of *Boswellia serrata* comprising from 30% to 90% AKBA, from 40% to 85% AKBA, from 50% to 80% AKBA, from 60% to 88% AKBA, or from 70% to 85% AKBA, to the patient;

wherein the composition further contains a live or lyophilized probiotic bacteria;

wherein the composition is administered at a dose sufficient to change the ratio between a first organism in the gut microbiome and a second organism in the gut microbiome, compared to a subject not treated with the composition. The live or lyophilized probiotic bacteria may be *Bifidobacterium pseudolongum.*

In various embodiments, methods of treating allergic pulmonary inflammation in a patient in need thereof include:

administering a first composition including AKBA or an extract of *Boswellia serrata* comprising from 30% to 90% AKBA, from 40% to 85% AKBA, from 50% to 80% AKBA, from 60% to 88% AKBA, or from 70% to 85% AKBA, to the patient; and administering a second composition including a live or lyophilized probiotic bacteria to the patient;

wherein the first and second compositions are administered at a dose sufficient to change the ratio between a first organism in the gut microbiome and a second organism in the gut microbiome, compared to a subject not treated with the composition.

Various embodiments relate to methods of maintaining diversity and/or increasing a percentage of *Bifidobacterium pseudolongum* in the gut microbiome of a patient in need thereof, by:

administering a composition comprising AKBA or an extract of *Boswellia serrata* comprising from 30% to 90% AKBA, from 40% to 85% AKBA, from 50% to 80% AKBA, from 60% to 88% AKBA, or from 70% to 85% AKBA, to the patient;

wherein the composition is administered at a dose sufficient to increase the percentage of *Bifidobacterium pseudolongum* in the gut microbiome, compared to a subject not treated with the composition. The composition may include AKBA or the extract of *Boswellia serrata* in combination with a live or lyophilized probiotic bacteria.

Various embodiments relate to methods of maintaining diversity and/or increasing a percentage of *Bifidobacterium pseudolongum* in the gut microbiome of a patient in need thereof, by:

administering a first composition comprising AKBA or an extract of *Boswellia serrata* comprising from 30% to 90% AKBA, from 40% to 85% AKBA, from 50% to 80% AKBA, from 60% to 88% AKBA, or from 70% to 85% AKBA, to the patient; and administering a second composition comprising a live or lyophilized probiotic bacteria to the patient;

wherein the first and second compositions are each administered at a dose sufficient to increase the percentage of *Bifidobacterium pseudolongum* in the gut microbiome, compared to a subject not treated with the composition. The composition may include AKBA or the extract of *Boswellia serrata* in combination with a live or lyophilized probiotic bacteria.

Various embodiments disclosed herein relate to a formulation for modulating a gut microbiome in a patient in need thereof, comprising:

a first composition comprising 3-O-acetyl-11-keto-b-boswellic acid (AKBA) or an extract of *Boswellia serrata* comprising from 30% to 90% AKBA; and a second composition comprising a live or lyophilized probiotic bacteria;

wherein the first and second compositions are each provided at a dose sufficient to change the ratio between a first organism in the gut microbiome and a second organism in the gut microbiome, compared to a subject not treated with the composition. The first and second compositions may be provided in a single dosage form, or in separate dosage forms.

BRIEF DESCRIPTION OF THE DRAWINGS

Reference will now be made to the accompanying drawings, which are not necessarily drawn to scale, and wherein.

DETAILED DESCRIPTION

Figure 1A:
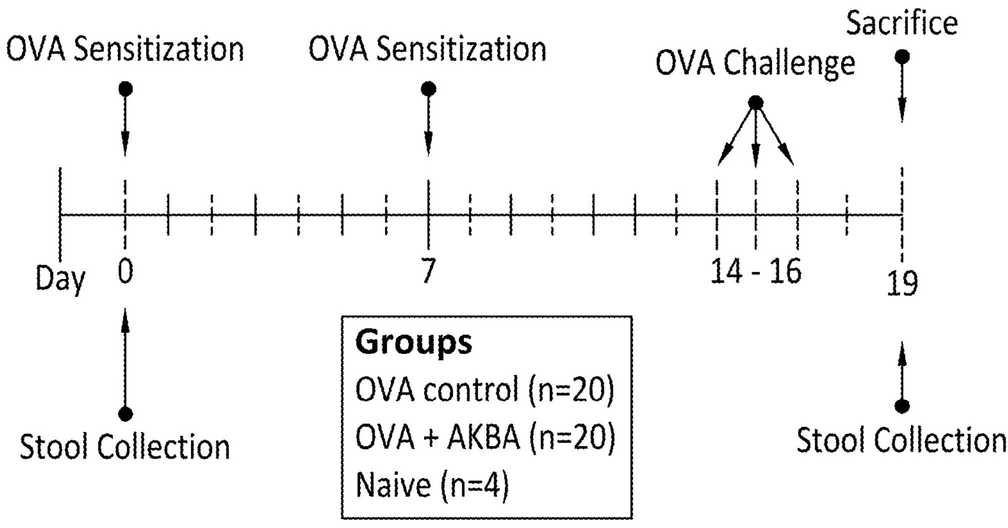
FIG. 1A shows the induction of allergic airway model, AKBA supplementation course and average weight (g) of mice and percent change following the duration of experiment. Colored lines corresponding to AKBA supplementation. Values in each column which have different letters are significantly different ($p<0.05$). (n=15).

Asthma is associated with significant morbidity. The gut microbiome has been shown to effect asthma development and exacerbation. Disclosed herein is an oral supplement containing *Boswellia serrata* (Indian frankincense) tree resin on allergic pulmonary inflammation and gut microbiome. An ovalbumin (OVA) based allergic airway model was used and mice were orally gavaged 100 mg/kg of *Boswellia serrata* as a supplementation throughout asthma sensitization and challenge. Treated mice showed significant weight loss, lower total lung leukocytes, eosinophil and Th2 cytokines, improved histology scoring and reduced reactivity to methacholine challenge. Asthmatic mice without *Boswellia serrata* supplementation showed a decrease in overall bacterial diversity, while treated mice were protected against loss. *Boswellia serrata* treated mice had a significant increase in *Bifidobacterium*, which was identified as *Bifidobacterium pseudolongum*. Oral administration of *B. pseudolongum* also reduced airway inflammation, suggesting it works as an anti-asthma agent via increases in *B. pseudolongum* from prebiotic influences.

The "gut-lung axis" is a theory which connects the gut microbiome to lung health [Frati, F. et al. The role of the microbiome in asthma: The gut-lung axis. Int. J. Mol. Sci. 20, 1-12 (2019)]. The gut microbiome in early life development, including a broad bacterial diversity, is critical in the maintenance of proper immune balance throughout life. Dysbiosis of the gut microbiome has been associated with allergies. Supplementation of probiotics (*Lactobacillus* and *Bifidobacterium*) have shown beneficial effects in allergic asthma in animal models. These probiotics are thought to modulate the host immune cells, including T helper Th2, Th17, regulatory T (Treg) cells and B cells, which are directly associated to allergic asthma. Commensal gut bacteria have been associated with decreased airway inflammation in animal model of asthma as well, including *Prevotella, Faecalibacterium* and *Akkermansia.*

The use of probiotics as a therapeutic strategy for asthma in humans is not conclusive. However, dietary interventions which selectively increase the abundance of microbes that provide metabolic benefits, such as short chain fatty acid production, is currently being investigated.

*Boswellia serrata* is a branching tree which produces a gum resin commonly known as Indian frankincense or olibanum. The plant is native to the dry regions of India and the Middle East. The resin has a rich, centuries long history, being used in serval parts of the world for medicinal proposes. The active compounds of the resins are thought to be the boswellic acids (BAs) (pentacyclic triterpenic acids). There are six different types of BAs, with 3-O-acetyl-11-keto-b-boswellic acid (AKBA) being most potent. The BAs target a variety of cancers, inflammatory and infectious diseases. BA have been shown to improve asthma phenotypes in mice models, and have also shown promising results in a small clinical trial. However, it is unclear what specific type of BAs were tested in these studies. BAs have been established as a multitargeting agent, modulating several targets, including enzymes (5-LOX), growth factors (Vascular endothelial growth factor), kinases (I-κ3 kinases), transcription factors (STAT3), receptors (DR4), and others related to the survival and proliferation of cells (Myeloid leukemia 1) [Roy, N. K. et al. An Update on Pharmacological Potential of Boswellic Acids against Chronic Diseases. *Int. J. Mol. Sci.* 2019, Vol. 20, Page 4101 20, 4101 (2019)]. Whether the gut microbiome is involved in the effect of BAs on asthma is unknown.

The most potent BA, 3-O-acetyl-11-keto-b-boswellic acid (AKBA), was discovered to have a prebiotic effect on the gut microbiome, specifically increasing *Akkermansia* and *Bifidobacterium* in healthy mice. In this study, an oral supplement of AKBA was found to attenuate allergic asthma using an OVA allergic airway model in BALB/cJ mice, and if this response is mediated by changes in the gut microbiome. AKBA was demonstrated to attenuate airway inflammation and improved airway hyperresponsiveness (AHR). This effect, at least partially, may be mediated by a specific bacterial species that is commonly found in pets, farm animals and other fur animals.

In an aspect, disclosed is a method for preventing or treating a disease or disorder in a subject in need thereof, wherein said disease or disorder is a disease associated with inflammation (for example, asthma or allergic diseases), the method comprising: administering to a subject a composition comprising a probiotic or a pharmaceutically acceptable derivative or salt thereof at a dose sufficient to increase a proportion of a *Bifidobacterium* compared to a subject not treated with the composition comprising the probiotic; wherein the probiotic comprises a therapeutically effective amount of *Bifidobacterium pseudolongum*. In certain embodiments, the *Bifidobacterium* comprises *Bifidobacterium pseudolongum*. In certain embodiments, the method further comprises co-administering a composition comprising *Boswellia serrata* (Indian frankincense) tree resin or a pharmaceutically acceptable derivative or salt thereof. In certain embodiments, the disease or disorder is inflammation in combination with the disease associated with inflammation, wherein the disease associated with inflammation is inflammatory bowel disease, rheumatoid arthritis, juvenile rheumatoid arthritis, psoriatic arthritis, osteoarthritis, refractory rheumatoid arthritis, chronic non-rheumatoid arthritis, osteoporosis or bone resorption, coronary heart disease, atherosclerosis, endothelial dysfunction, vasculitis, ulcerative colitis, psoriasis, adult respiratory distress syndrome, diabetes, delayed-type hypersensitivity in skin disorders, asthma, endothelial dysfunction, or a combination thereof. In certain embodiments, the disease associated with inflammation is asthma. In certain embodiments, the therapeutically effective amount of the *Bifidobacterium pseudolongum* is effective to modulate expression or production of at least one inflammatory marker selected from the group consisting of 5-lipoxygenase (5-LOX), 5-Lipoxygenase activating protein (FLAP), Macrophage/Adipocyte Fatty acid binding protein (aP2), IFN-γ, IL-4, ICAM, VCAM, MMPs, TNFα and IL-1β. In certain embodiments, the composition is administered orally. In certain embodiments, the subject is human.

In an aspect, disclosed is a method for preventing or treating a disease or disorder in a subject in need thereof, wherein said disease or disorder is a disease associated with inflammation (for example, asthma or allergic diseases), the method comprising administering to the subject a therapeutically effective amount of *Bifidobacterium pseudolongum*. In certain embodiments, the disease or disorder is inflammation in combination with the disease associated with inflammation, wherein the disease associated with inflammation is inflammatory bowel disease, rheumatoid arthritis, juvenile rheumatoid arthritis, psoriatic arthritis, osteoarthritis, refractory rheumatoid arthritis, chronic non-rheumatoid arthritis, osteoporosis or bone resorption, coronary heart disease, atherosclerosis, endothelial dysfunction, vasculitis, ulcerative colitis, psoriasis, adult respiratory distress syndrome, diabetes, delayed-type hypersensitivity in skin disorders, asthma, endothelial dysfunction, or a combination thereof. In certain embodiments, the disease associated with inflammation is asthma. In certain embodiments, the therapeutically effective amount of *Bifidobacterium pseudolongum* is effective to modulate expression or production of at least one inflammatory marker selected from the group consisting of 5-lipoxygenase (5-LOX), 5-Lipoxygenase activating protein (FLAP), Macrophage/Adipocyte Fatty acid binding protein (aP2), IFN-γ, IL-4, ICAM, VCAM, MMPs, TNFα and IL-1β. In certain embodiments, the method further comprises co-administering a composition comprising *Boswellia serrata* (Indian frankincense) tree resin or a pharmaceutically acceptable derivative or salt thereof. In certain embodiments, the method increases a proportion of a *Bifidobacterium* compared to a subject not treated with the therapeutically effective amount of *Bifidobacterium pseudolongum*. In certain embodiments, the *Bifidobacterium* comprises *Bifidobacterium pseudolongum*. In certain embodiments, the therapeutically effective amount of *Bifidobacterium pseudolongum* is administered orally. In certain embodiments, the subject is human.

In an aspect, disclosed is a composition for preventing or treating a disease or disorder in a subject in need thereof, wherein said disease or disorder is a disease associated with inflammation, the composition comprising a probiotic or a pharmaceutically acceptable derivative or salt thereof; wherein the probiotic comprises a therapeutically effective amount of *Bifidobacterium pseudolongum*. In certain embodiments, the composition increases a proportion of a *Bifidobacterium* compared to a subject not treated with the composition comprising the probiotic or a pharmaceutically acceptable derivative or salt thereof. In certain embodiments, the *Bifidobacterium* comprises *Bifidobacterium pseudolongum*. In certain embodiments, the composition is co-administered with a composition comprising *Boswellia serrata* (Indian frankincense) tree resin or a pharmaceutically acceptable derivative or salt thereof. In certain embodiments, the composition is administered orally. In certain embodiments, the subject is human.

In an aspect, disclosed is a composition for preventing or treating a disease or disorder in a subject in need thereof, wherein said disease or disorder is a disease associated with inflammation, the composition comprising a therapeutically effective amount of *Bifidobacterium pseudolongum*. In certain embodiments, the disease or disorder is inflammation in combination with the disease associated with inflammation, wherein the disease associated with inflammation is inflammatory bowel disease, rheumatoid arthritis, juvenile rheumatoid arthritis, psoriatic arthritis, osteoarthritis, refractory rheumatoid arthritis, chronic non-rheumatoid arthritis, osteoporosis or bone resorption, coronary heart disease, atherosclerosis, endothelial dysfunction, vasculitis, ulcerative colitis, psoriasis, adult respiratory distress syndrome, diabetes, delayed-type hypersensitivity in skin disorders, asthma, endothelial dysfunction, or a combination thereof. In certain embodiments, the disease associated with inflammation is asthma. In certain embodiments, the composition is effective to modulate expression or production of at least one inflammatory marker selected from the group consisting of 5-lipoxygenase (5-LOX), 5-Lipoxygenase activating protein (FLAP), Macrophage/Adipocyte Fatty acid binding protein (aP2), IFN-γ, IL-4, ICAM, VCAM, MMPs, TNFα and IL-1β. In certain embodiments, the composition increases a proportion of a *Bifidobacterium* compared to a subject not treated with the composition comprising the therapeutically effective amount of *Bifidobacterium pseudolongum*. In certain embodiments, the *Bifidobacterium* comprises *Bifidobacterium pseudolongum*. In certain embodiments, the composition is co-administered with a composition comprising *Boswellia serrata* (Indian frankincense) tree resin or a pharmaceutically acceptable derivative or salt thereof. In certain embodiments, the composition is administered orally. In certain embodiments, the subject is human.

In an aspect, disclosed is a composition for treating or preventing asthma in a subject comprising a probiotic or a pharmaceutically acceptable derivative or salt thereof; wherein the probiotic comprises a therapeutically effective amount of *Bifidobacterium pseudolongum*. In certain embodiments, the composition increases a proportion of a *Bifidobacterium* compared to a subject not treated with the composition comprising the probiotic or a pharmaceutically acceptable derivative or salt thereof. In certain embodiments, the *Bifidobacterium* comprises *Bifidobacterium pseudolongum*. In certain embodiments, the composition is co-administered with a composition comprising *Boswellia serrata* (Indian frankincense) tree resin or a pharmaceutically acceptable derivative or salt thereof. In certain embodiments, the composition is administered orally. In certain embodiments, the subject is human.

In an aspect, disclosed is a composition for treating or preventing asthma in a subject, the composition comprising a therapeutically effective amount of *Bifidobacterium pseudolongum*. In certain embodiments, the therapeutically effective amount of *Bifidobacterium pseudolongum* is co-administered with a composition comprising *Boswellia serrata* (Indian frankincense) tree resin or a pharmaceutically acceptable derivative or salt thereof. In certain embodiments, the composition increases a proportion of a *Bifidobacterium* compared to a subject not treated with the composition comprising the probiotic or a pharmaceutically acceptable derivative or salt thereof. In certain embodiments, the *Bifidobacterium* comprises *Bifidobacterium pseudolongum*. In certain embodiments, the composition is administered orally. In certain embodiments, the subject is human.

In an aspect, disclosed is a method of producing a composition for preventing or treating a disease or disorder in a subject in need thereof, wherein said disease or disorder is a disease associated with inflammation (for example, asthma or allergic diseases), the method comprising: providing a lyophilized probiotic bacteria that comprises *Bifidobacterium pseudolongum*; and providing a carrier that comprises at least one pharmaceutically acceptable excipient that is mixed with the live or lyophilized probiotic bacteria in a pharmaceutically effective amount sufficient to increase a proportion of a *Bifidobacterium*. In certain embodiments, the *Bifidobacterium* comprises *Bifidobacterium pseudolongum.*

In an aspect, disclosed is a method of producing a composition for preventing or treating asthma, the method comprising: providing a live or lyophilized probiotic bacteria that comprises *Bifidobacterium pseudolongum*; and providing a carrier that comprises at least one pharmaceutically acceptable excipient that is mixed with the live or lyophilized probiotic bacteria in a pharmaceutically effective amount sufficient to increase a proportion of a *Bifidobacterium*. In certain embodiments, the *Bifidobacterium* comprises *Bifidobacterium pseudolongum.*

In an aspect, disclosed is a composition for inducing or supporting weight loss, or preventing or reducing weight gain in a subject, the composition comprising a probiotic or a pharmaceutically acceptable derivative or salt thereof; wherein the probiotic comprises a therapeutically effective amount of *Bifidobacterium pseudolongum*. In certain embodiments, the composition further comprises a carrier that comprises at least one pharmaceutically acceptable excipient. In certain embodiments, the composition is co-administered with a composition comprising a probiotic or a pharmaceutically acceptable derivative or salt thereof; wherein the probiotic comprises a therapeutically effective amount of 3-O-acetyl-11-keto-b-boswellic acid (AKBA) or a pharmaceutically acceptable derivative or salt thereof. In certain embodiments, the composition is administered orally. In certain embodiments, the subject is human.

In an aspect, disclosed is a composition for inducing or supporting weight loss, or preventing or reducing weight gain in a subject, the composition comprising a probiotic or a pharmaceutically acceptable derivative or salt thereof; wherein the probiotic comprises a therapeutically effective amount of 3-O-acetyl-11-keto-□-boswellic acid (AKBA) or a pharmaceutically acceptable derivative or salt thereof. In certain embodiments, the composition further comprises a carrier that comprises at least one pharmaceutically acceptable excipient. In certain embodiments, the composition is co-administered with a composition comprising a probiotic or a pharmaceutically acceptable derivative or salt thereof; wherein the probiotic comprises a therapeutically effective amount of *Bifidobacterium pseudolongum*. In certain embodiments, the composition is administered orally. In certain embodiments, the subject is human.

In an aspect, disclosed is a composition for inducing or supporting weight loss, or preventing or reducing weight gain in a subject, the composition comprising a probiotic or a pharmaceutically acceptable derivative or salt thereof; wherein the probiotic comprises a therapeutically effective amount of *Bifidobacterium pseudolongum*, and a therapeutically effective amount of 3-O-acetyl-11-keto-b-boswellic acid (AKBA) or a pharmaceutically acceptable derivative or salt thereof. In certain embodiments, the composition further comprises a carrier that comprises at least one pharmaceutically acceptable excipient. In certain embodiments, the composition is administered orally. In certain embodiments, the subject is human.

In an aspect, disclosed is a composition for inducing or supporting weight loss, or preventing or reducing weight gain in a subject, the composition comprising a therapeutically effective amount of *Bifidobacterium pseudolongum*. In certain embodiments, the composition is co-administered with a composition comprising a therapeutically effective amount of 3-O-acetyl-11-keto-b-boswellic acid (AKBA) or a pharmaceutically acceptable derivative or salt thereof. In certain embodiments, the composition further comprises a carrier that comprises at least one pharmaceutically acceptable excipient. In certain embodiments, the composition is administered orally. In certain embodiments, the subject is human.

In an aspect, disclosed is a composition for inducing or supporting weight loss, or preventing or reducing weight gain in a subject, the composition comprising a therapeutically effective amount of 3-O-acetyl-11-keto-b-boswellic acid (AKBA) or a pharmaceutically acceptable derivative or salt thereof. In certain embodiments, the composition is co-administered with a composition comprising a therapeutically effective amount of *Bifidobacterium pseudolongum*. In certain embodiments, the composition further comprises a carrier that comprises at least one pharmaceutically acceptable excipient. In certain embodiments, the composition is administered orally. In certain embodiments, the subject is human.

In an aspect, disclosed is a composition for inducing or supporting weight loss, or preventing or reducing weight gain in a subject, the composition comprising a therapeutically effective amount of *Bifidobacterium pseudolongum*, and a therapeutically effective amount of 3-0-acetyl-11-keto-b-boswellic acid (AKBA) or a pharmaceutically acceptable derivative or salt thereof. In certain embodiments, the composition further comprises a carrier that comprises at least one pharmaceutically acceptable excipient. In certain embodiments, the composition is administered orally. In certain embodiments, the subject is human.

In an aspect, disclosed is a method for inducing or supporting weight loss, or preventing or reducing weight gain in a subject, the method comprising: administering to a subject a composition comprising a probiotic or a pharmaceutically acceptable derivative or salt thereof at a dose sufficient to increase a proportion of a *Bifidobacterium* compared to a subject not treated with the composition comprising the probiotic; wherein the probiotic comprises a therapeutically effective amount of *Bifidobacterium pseudolongum*. In certain embodiments, the method further includes co-administering a composition comprising a probiotic or a pharmaceutically acceptable derivative or salt thereof; wherein the probiotic comprises a therapeutically effective amount of 3-0-acetyl-11-keto-b-boswellic acid (AKBA) or a pharmaceutically acceptable derivative or salt thereof. In certain embodiments, the method comprises administering the composition orally. In certain embodiments, the subject is human.

In an aspect, disclosed is a method for inducing or supporting weight loss, or preventing or reducing weight gain in a subject, the method comprising: administering to a subject a composition comprising a probiotic or a pharmaceutically acceptable derivative or salt thereof; wherein the probiotic comprises a therapeutically effective amount of 3-O-acetyl-11-keto-b-boswellic acid (AKBA) or a pharmaceutically acceptable derivative or salt thereof. In certain embodiments, the method further includes co-administering a composition comprising a probiotic or a pharmaceutically acceptable derivative or salt thereof at a dose sufficient to increase a proportion of a *Bifidobacterium* compared to a subject not treated with the composition comprising the probiotic; wherein the probiotic comprises a therapeutically effective amount of *Bifidobacterium pseudolongum*. In certain embodiments, the method comprises administering the composition orally. In certain embodiments, the subject is human.

In an aspect, disclosed is a method for inducing or supporting weight loss, or preventing or reducing weight gain in a subject, the method comprising: administering to a subject a composition comprising a probiotic or a pharmaceutically acceptable derivative or salt thereof; wherein the probiotic comprises a therapeutically effective amount of *Bifidobacterium pseudolongum*, and a therapeutically effective amount of 3-O-acetyl-11-keto-b-boswellic acid (AKBA) or a pharmaceutically acceptable derivative or salt thereof. In certain embodiments, the method comprises administering the composition orally. In certain embodiments, the subject is human.

In an aspect, disclosed is a method for inducing or supporting weight loss, or preventing or reducing weight gain in a subject, the method comprising: administering to a subject a composition comprising a therapeutically effective amount of *Bifidobacterium pseudolongum*. In certain embodiments, the method further includes co-administering a comprising a therapeutically effective amount of 3-O-acetyl-11-keto-b-boswellic acid (AKBA) or a pharmaceutically acceptable derivative or salt thereof. In certain embodiments, the method comprises administering the composition orally. In certain embodiments, the subject is human In an aspect, disclosed is a method for inducing or supporting weight loss, or preventing or reducing weight gain in a subject, the method comprising: administering to a subject a composition comprising a therapeutically effective amount of 3-O-acetyl-11-keto-b-boswellic acid (AKBA) or a pharmaceutically acceptable derivative or salt thereof. In certain embodiments, the method further includes co-administering a composition comprising a therapeutically effective amount of *Bifidobacterium pseudolongum*. In certain embodiments, the method comprises administering the composition orally. In certain embodiments, the subject is human.

In an aspect, disclosed is a method for inducing or supporting weight loss, or preventing or reducing weight gain in a subject, the method comprising: administering to a subject a composition comprising a therapeutically effective amount of *Bifidobacterium pseudolongum*, and a therapeutically effective amount of 3-O-acetyl-11-keto-b-boswellic acid (AKBA) or a pharmaceutically acceptable derivative or salt thereof. In certain embodiments, the method comprises administering the composition orally. In certain embodiments, the subject is human In an aspect, disclosed is a method of producing a composition for inducing or supporting weight loss, or preventing or reducing weight gain in a subject, the method comprising: providing a live or lyophilized probiotic bacteria that comprises a therapeutically effective amount of *Bifidobacterium pseudolongum*; and providing a carrier that comprises at least one pharmaceutically acceptable excipient that is mixed with the live or lyophilized probiotic bacteria in a pharmaceutically effective amount sufficient to increase a proportion of a *Bifidobacterium*. In certain embodiments, the subject is human.

In an aspect, disclosed is a method of producing a composition for inducing or supporting weight loss, or preventing or reducing weight gain in a subject, the method comprising: providing a lyophilized probiotic bacteria that comprises a therapeutically effective amount of *Bifidobacterium pseudolongum*; providing a therapeutically effective amount of 3-O-acetyl-11-keto-b-boswellic acid (AKBA) or a pharmaceutically acceptable derivative or salt thereof; and providing a carrier that comprises at least one pharmaceutically acceptable excipient that is mixed with the lyophilized probiotic bacteria and 3-O-acetyl-11-keto-b-boswellic acid (AKBA) or a pharmaceutically acceptable derivative or salt thereof in a pharmaceutically effective amount sufficient to increase a proportion of a *Bifidobacterium*. In certain embodiments, the subject is human.

The present disclosure provides compositions including a probiotic comprising an appropriate quantity of *Bifidobacterium pseudolongum*, as well as a system and methods for using the disclosed probiotic composition to prevent or treat inflammatory diseases such as asthma, and/or to induce and sustain weight loss in subjects, such as humans, horses, rats, mice, ruminants, primates, monkeys, hamsters, rabbits, cats and various avian and fish species. The disclosed probiotic composition may be administered to a subject to increase the population of *Bifidobacterium pseudolongum* in the gastrointestinal tract of the host. Without wishing to be bound by this theory it is believed that successful establishment and propagation of *Bifidobacterium pseudolongum* in the gastrointestinal tract of a subject may induce and/or support beneficial weight loss and or reduce airway inflammation.

*Bifidobacterium pseudolongum* may be received in a carrier to facilitate delivery to a subject in need thereof. As used herein, the term "carrier" is intended to broadly refer to any substance (e.g., a tableting agent or a liquid) or article (e.g., a capsule shell or a polymer matrix) that facilitates administration of *Bifidobacterium pseudolongum* by providing a medium for its conveyance to the consuming subject. "Carrier" means a diluent, excipient, or vehicle with which an active compound is administered. A "pharmaceutically acceptable carrier" means a substance, e.g., excipient, diluent, or vehicle, that is useful in preparing a pharmaceutical composition that is generally safe, non-toxic and neither biologically nor otherwise undesirable, and includes a carrier that is acceptable for veterinary use as well as human pharmaceutical use. A "pharmaceutically acceptable carrier" includes both one and more than one such carrier. Those skilled in the art will appreciate that the carrier should be substantially non-toxic in the amounts employed and should not significantly inhibit the intended probiotic value of *Bifidobacterium pseudolongum* in the composition.

The *Bifidobacterium pseudolongum* bacteria useful in the disclosed compositions and methods may be provided as a live culture, as a dormant material or a combination thereof. Those skilled in the art will appreciate that the *Bifidobacterium pseudolongum* bacteria may be rendered dormant by, for example, a lyophilization process, as is well known to those skilled in the art. An example of an appropriate lyophilization process may begin with a media carrying appropriate *Bifidobacterium* bacteria to which an appropriate protectant may be added for cell protection prior to lyophilization. Examples of appropriate protectants include, but are not limited to, distilled water, polyethylene glycol, sucrose, trehalose, skim milk, xylose, hemicellulose, pectin, amylose, amylopectin, xylan, arabinogalactan, starch (e.g., potato starch or rice starch) and polyvinylpyrrolidone. Gasses useful for the lyophilization process include but are not limited to nitrogen and carbon dioxide.

The disclosed compositions may be administered to a subject to prevent or treat inflammation, such as respiratory inflammation (for example, asthma), and/or to induce weight loss pursuant to an appropriate cleansing and inoculation protocol. Furthermore, the disclosed compositions may be used to sustain weight loss in the subject pursuant to an appropriate inoculation and maintenance protocol or to prevent or treat respiratory inflammation such as asthma. the disclosed compositions and/or methods may be used in coordination with a regime of one or more other compositions and/or methods used to sustain weight loss in the subject pursuant to an appropriate inoculation and maintenance protocol or to prevent or treat respiratory inflammation such as asthma.

It will be understood, however, that the specific dose level for any particular subject will depend upon a variety of factors including the activity of the specific compound employed, the age, body weight, general health, sex, diet, time of administration, route of administration, and rate of excretion, drug combination and the severity of the particular disease undergoing therapy.

In one aspect, *Bifidobacterium pseudolongum* in the disclosed probiotic composition may be provided as a dispersion in a solution or media. In another aspect, the *Bifidobacterium pseudolongum* in the disclosed probiotic composition may be provided as a semi-solid or cake. In another aspect, *Bifidobacterium pseudolongum* in the disclosed probiotic composition may be provided in powdered form.

The disclosed compositions may be prepared in various forms, such as capsules, suppositories, tablets, food drink and the like. Optionally, the disclosed compositions may include various pharmaceutically acceptable excipients, such as microcrystalline cellulose, mannitol, glucose, defatted milk powder, polyvinylpyrrolidone, starch and combinations thereof.

The concentration of *Bifidobacterium pseudolongum* in the disclosed composition may vary depending upon the desired result, the type of bacteria used, the form and method of administration, among other things. For example, a probiotic composition may be prepared having a count of *Bifidobacterium pseudolongum* in the preparation of no less than about $1\times10^6$ colony forming units per gram, based upon the total weight of the preparation.

The present disclosure is illustrated and further described in more detail with reference to the following non-limiting examples.

EXAMPLES

Materials and Methods

Induction of Allergic Airway Model and AKBA Supplement

Eight-week-old BALB/cJ female mice were purchased from the Jackson Laboratory (Bar Harbor, ME, US) and housed in plastic cages with corncob bedding at the University of Connecticut Health (Farmington, CT.). Animal rooms maintained a 12-h light/dark cycle and were pathogen free. Mice were fed a 18% protein rodent diet (18.6% protein, 6.2% fat, 44.2% carbohydrate, 3.5% soluble fiber, 14.7% total fiber, 5.3% ash) purchased from Envigo (Indianapolis, IN, US) and supplied autoclaved water.

Allergic airway phenotype was induced by using an ovalbumin (OVA, hen egg) sensitization and challenge model as previously described with modifications [Beigelman, A. et al. Azithromycin attenuates airway inflammation in a noninfectious mouse model of allergic asthma. *Chest* 136, 498-506 (2009)]. Briefly (FIG. 1), two groups of mice (OVA control and OVA+AKBA) were sensitized with intraperitoneal ovalbumin plus alum on days 0 and 7, challenged for 3 days (day 14 to day 17) via nebulized OVA at 1% in PBS for 30 mins, and harvested 48 hr after final challenge. Supplementation groups (OVA+AKBA) were given 100 mg/kg of water soluble AKBA (pH 7) (PLT Health Solutions, Morristown, NJ, US) in autoclaved mouse water, via gavage, every other day for 10 days and then every day for the remainder of the experiment (9 days). OVA control and naïve mouse continued to receive normal autoclaved mouse water. Mice were weighted at the beginning and end of the experiment. Experiments involving AKBA were conducted twice, with the first group containing 5 mice per group and the second containing 15 mice per group (5 per group for naive). Experiment procedures were identical, and results were pooled for n=20 (n=5 for naive). Animal protocol 102063-0522 was approved by the University of Connecticut Health IACUC board.

Repetition of Experimental Procedures with *B. pseudolongum* Supplement

Experiments were repeated, as stated above, with oral gavages of *B. pseudolongum* culture in place of AKBA supplementation. Groups were designated as OVA control (n=10), OVA+*B. pseudolongum* (n=10) and naïve (n=5). OVA+*B. pseudolongum* groups were given $10^8$ CFU *B. pseudolongum* in culture medium via gavage, every other day for 10 days and then every day for the remainder of the experiment (9 days).

BAL, Blood, and Lung Tissue Collection

Serum was obtained through blood collect from mice via cardiac puncture at the time of sacrifice (euthanized with 150 mg/kg ketamine and 10 mg/kg xylazine) and was allowed to clot for a minimum of 30 minutes. Clotted blood was spun down at 1500×g for 15 min. Serum was isolated and stored at −80° C. until further analysis. To obtain broncho-alveolar lavage (BAL) fluid cells from the mice, lungs were lavaged with 2 mL of saline. BAL cells were pelleted at 500×g for 5 min at 4° C. Red lysis buffer was used to remove any residual red blood cells. Cell free fluid was saved separately and stored at −80° C. Total cell counts were taken manually using a hemocytometer. Cytospin preparations were fixed in methanol and stained using May-Grunwald and counter stained with Giemsa. For histopathologic assessment, the left lungs were removed and fixed with 4% buffered formalin for 72 h and then placed in 70% ETOH.

Flow Cytometry and IgE

Multiple inflammatory mediators were analyzed in the cell-free supernatant of BAL fluid using a multiplex flow-cytometry based assay according to manufacturer's recommendations (BioLegend, San Diego, CA, US). Volume of cell free fluid was concentrated using a 50K centrifugal filter spun at 3000 g for 10-15 minutes. Samples were run on a ZE5 Cell Analyzer (Bio-Rad, Hercules, CA, US) and sample processing was conducting using software provided from the kit's manufacturer (BioLegend, San Diego, CA, US). Serum specific ovalbumin IgE levels was detected by using an ELISA kit with a sensitivity of 3.8 ng/mL per manufacturer's protocol (Cayman Chemical Company, Ann Arbor, MI, US).

Tissue Histology and Scoring

Lung sectioning and staining was performed by the UConn Health Research Histology Core (Farmington, CT, US). Formalin-fixed, paraffin-embedded lungs were sectioned and stained with hematoxylin and eosin (for gross pathology) and periodic acid-Schiff with hematoxylin counterstain (for mucus production). Sections from the left lung were evaluated in their entirety and representative were images taken. Pathologic scoring was performed as described previously[20]. Briefly, a blinded pulmonologist graded each stain using a light microscope. For inflammation scores, 0 corresponded to no detectable inflammation; 1 to mild peribronchiolar/perivascular cuffing with inflammatory cells; 2 to significant peribronchiolar/perivascular clustering; and 3 to significant clustering and airway remodeling (e.g., smooth muscle hypertrophy and hyperplasia). For mucus scores, 0 corresponded to no visible mucus; 1 to occasional and punctate mucus staining in the airways; 2 to presence of ring-like mucus structures in <10% of airways; and 3 to presence of ring-like mucus structures in >10% of airways. Half scores were permitted.

Measurement of Airway Hyperresponsiveness

Airway reactivity was assessed based on total respiratory system resistance (Rrs) response to increasing doses (0-100 mg/ml) of acetyl-β-methacholine chloride (Sigma-Aldrich, St. Louis, MO). Mice were euthanized (150 mg/kg ketamine and 10 mg/kg xylazine), underwent tracheostomies and were mechanically ventilated using the flexiVent system (SCIREQ, Montreal, CA). Airway reactivity was determined by assessing forced oscillatory mechanics every 10 s for 4 min following each methacholine challenge.

Sample Collection, DNA Extraction and 16S rRNA Amplification and Sequencing

Fresh fecal pellets were collected upon defecation and stored in sterile RNA-/DNA-/RNAse-/DNAse-free microcentrifuge tubes at the beginning and end of experiment (FIG. 1). Collected pellets were placed at −80° C. for storage following collection. DNA from pellets were extracted using the PowerSoil DNA Isolation Kit (Qiagen, Hilden, Germany) according to the manufacturer's protocol. Amplicon library preparation and V4 region of 16S rRNA gene sequencing were performed at Illumina HiSeq 4000 (Illumina, CA, US) platform.

Processing of the 16S rRNA Sequences

Raw 16S rRNA sequences (150-bp paired-end reads) were initially processed by BaseSpace software (Illumina, CA, US). One mismatch in primer and zero mismatch in barcodes were applied to sample deconvolution. Deconvoluted sequences were further processed using the DADA2 data processing pipeline with default parameters to obtain amplicon sequence variants (ASVs). Final taxonomic assignment was conducted using RDP-classifier (v2.11) with 0.5 confidence value as cut-off. Reads with <0.5 confidence of classification was "unclassified" at a given taxonomical level.

*Bifidobacterium* Isolation and Identification

Mouse feces stored at −80° C. were thawed and mixed with 1 mL sterile peptone water. Subsequent 1:10 and 1:100 dilutions were made using the suspended fecal slurry and sterile peptone water. Approximately 1500_, was introduced to *Bifidobacterium*-specific medium (BSM) agar containing 55 g/L DeMann Rogosa-Sharpe agar (BD Difco, NJ, US), 15 g/L agar, 0.5% (wt/vol) L-cysteine hydrochloride (Sigma-Aldrich, MO, US), and 0.5% (wt/vol) mupirocin (AppliChem Panreac, IA, US) to select for Bifidobacteria. Agar plates were incubated for 48 h at 37° C. in anaerobic conditions (7% Hz, 10% $CO_2$, $N_2$ balance) (Coy Labs, MI, USA). Individual colonies were selected and grown on BSM plates under the same conditions. Upon confirmation of uniform colony morphology, individual colonies were selected and grown on MRS plates supplemented with 0.5% (wt/vol) L-cysteine hydrochloride under the same conditions. Individual colonies were selected from MRS plates and grown in MRS broth supplemented with 0.5% (wt/vol) L-cysteine hydrochloride for 14 h under the same conditions. Liquid cultures were preserved as 25% (vol/vol) glycerol freezer stocks at −80° C. Isolated liquid cultures were extracted using the Quick-DNA Fungal/Bacterial Kits (Zymo, Irvine, CA, US).

Following extract, DNA was amplified using a qPCR Master Mix (New England Biolabs, Ipswich, MA) and ITS targeted primers (Forward—CAAGGCCATCAACTGGTTCA and Reverse ACGTCGTGCTGCTCGAATGT) using cycling conditions of 95° C. for 3 min, 25 cycles of 95° C. for 30 secs, 55° C. for 30 secs and 72° C. for 1 min and then a final extension of 72° C. for 5 min. Samples were cleaned using a PCR cleanup kit (Qiagen, Hilden, Germany) and sent to Genewiz (South Plainfield, NJ, US) for sanger sequencing. Species identification was then confirmed using sequence files in Basic Local Alignment Search Tool software (GenBank, NIH, Bethesda MD, US) against the NCBI Reference Sequence database.

Analysis of Immune Responses

Means from the groups were analyzed for statistical significance by using the Mann-Whitney test, one-way analysis of variance or an unpaired t-tests. The significance level for tests included $p<0.05$ and were preformed using Prism 7 (GraphPad Software, La Jolla, CA).

Analysis of 16S rRNA Sequencing Data

ASV counts were converted to relative abundance and agglomerated at the phylum and genus levels using the Phyloseq R package to visualize the microbiome composition in a stacked bar plot. All 10 phyla were included in the bar plot at phylum level, while the most abundant 24 genera were displayed in the bar plot at genus level, with additional genera being grouped together in a $25^{th}$ "other" category. Sample reads were rarefied to 10,000 reads to account for uneven sampling depth. Alpha diversity was determined with the richness and Shannon diversity metrics at the ASV level. Wilcoxon sum rank test was performed to compare alpha diversity of stool microbiome between asthma control and AKBA treated mice at day 0 and day 19. Beta diversity was visualized by principal component analysis (PCA). DESeq2, with an adjusted p value<0.05, was used for the differential taxa analysis. All plots were created with "ggplot2" and all analyses were conducted in RStudio version 4.1.0.

Results

Figure 1B:
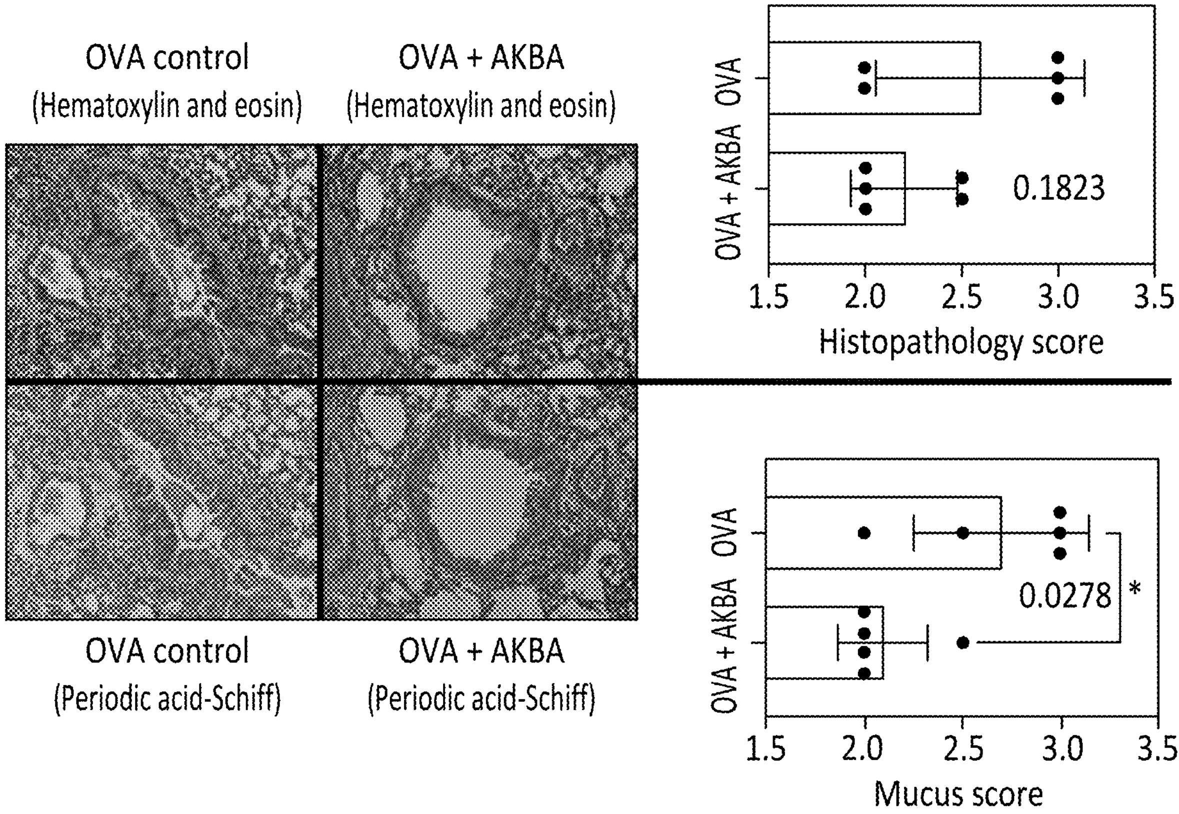
FIG. 1B shows representative pictures of both OVA control and OVA+AKBA lung histology and scoring (n=5 mice/group).

AKBA Supplementation Decreased Weight and the Severity of Tissue Inflammation in the Lungs Mice were given 100 mg/kg of AKBA enterally as described (FIG. 1A) and experienced a significant decrease in weight when compared to both the OVA control group and naïve group (unpaired t-test, p=<0.0001) (FIG. 1A). OVA+AKBA saw a total average loss of −2.32±4.19% of starting weight while the OVA control and naïve group saw a positive weight gain of 8.36±6.18% and 5.04±0.71% respectively.

OVA exposure led to evidence of peribranchial/perivascular and inflammation in the lungs (FIG. 1B), specifically clusters of inflammatory cells surrounding the airways, mucus buildup and airway smooth muscle. Blinded comparison of the inflammation and airway smooth muscle remodeling revealed that OVA+AKBA mice had slightly less severe histopathologic changes than OVA control mice (2.0±0.49 vs. 2.5±0.24, unpaired t-test, p=0.1823). However, the OVA+AKBA animals showed a significantly lower mucus production in mucus scoring (2.0±0.4 vs. 2.5±0.2, unpaired t-test, p=0.0278).

Figure 1C:
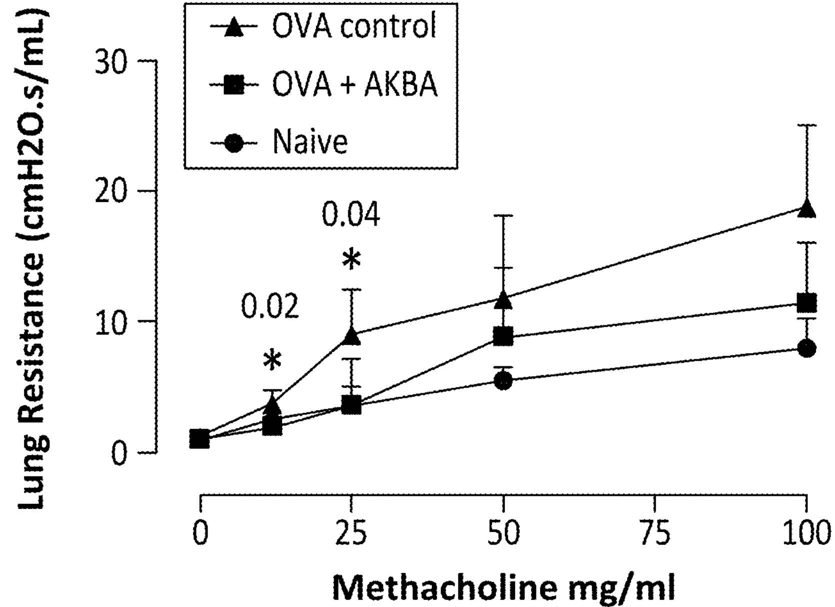
FIG. 1C shows a total respiratory system resistance (Rrs) following increasing doses of aerosolized methacholine. Data represent mean±SD. n=4 all groups. *Significant differences are labeled for OVA control vs. OVA+AKBA mean.

AKBA Attenuated Ovalbumin-Dependent Allergic Airway Inflammation with Decreased Airway Hyper-Reactivity Exposure to OVA induced allergic airway disease caused airway hyper-reactivity and bronchoconstriction in response to the receptor agonist methacholine (FIG. 1C). No significant difference was seen between all three groups at 0 mg/mL (ANOVA test, p=0.341). Experimental assessment of respiratory function using the FlexiVent system revealed that OVA+AKBA animals had significantly lower increases in total respiratory system resistance in response to methacholine challenge when compared to OVA control animals at 12.5 mg (2.38±0.55 vs 4.65±0.94, unpaired t-test, p=0.02) and 25 mg (3.56±1.25 vs 9.01±3.07, unpaired t-test, p=0.04). No significant difference was found between OVA control and OVA+AKBA at higher concentrations. However, trends are seen with OVA+AKBA having lower averages of lung resistance when compared to the OVA control group. Naïve mice were significantly less reactive than the OVA control group at concentrations of 12.5 mg/mL (unpaired t-test, p=0.02), 25 mg/mL (unpaired t-test, p=0.03) and 100 mg/mL (unpaired t-test, p=0.03). Importantly, the OVA+AKBA groups was not significantly different from control groups at any concentration.

Figure 2A:
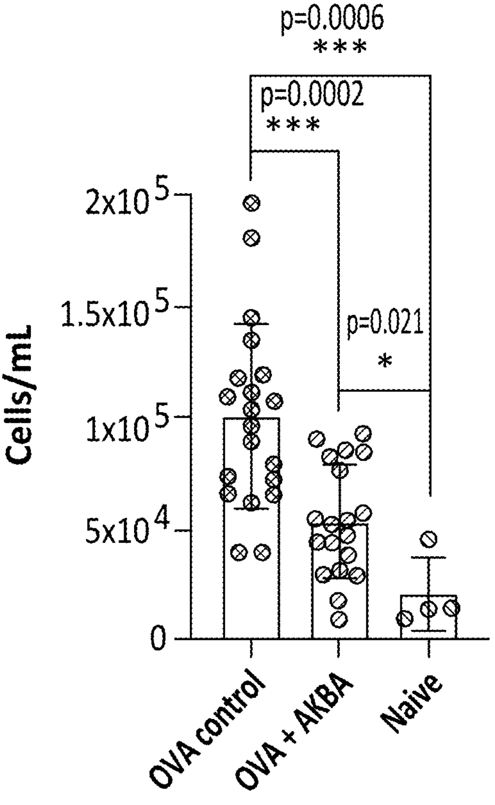
FIG. 2A shows the results when BAL fluid was analyzed for total cell number in three groups of mice. The analysis was performed as follows: mice that were sensitized and challenged with ova (column 1) (n=20); mice that were sensitized and challenged with ova and treated with AKBA solution (column 2) (n=19); naive mice (column 3) (n=4); Values represent mean±SD.

AKBA Attenuated Ovalbumin-Dependent Allergic Airway Inflammation with Decreased Concentrations of Inflammation Markers Our allergic airways model was able to produce elevated white blood cells in the BAL of all mice sensitized and challenged with OVA. The OVA control group of mice had 78.88% (Mann-Whitney test, p=0.0008) more leukocyte counts than the naïve group. Total leukocyte counts were significantly lower in those given 100 mg/kg AKBA versus the OVA control group by 46.69% (Mann-Whitney test, p=0.0002)(FIG. 2A). However, the AKBA group had higher counts than the naïve control, by 60.38% (Mann-Whitney test, p=0.0212).

Figure 2B:
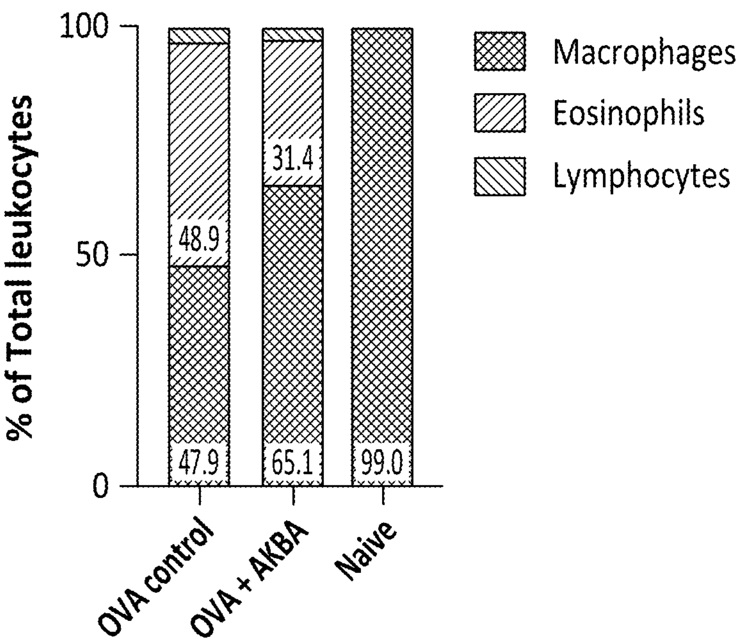
FIG. 2B is a graph showing results when Cell differentiations were averaged and based on percentage (naïve n=4, OVA control and OVA+AKBA=20).
Figure 2C:
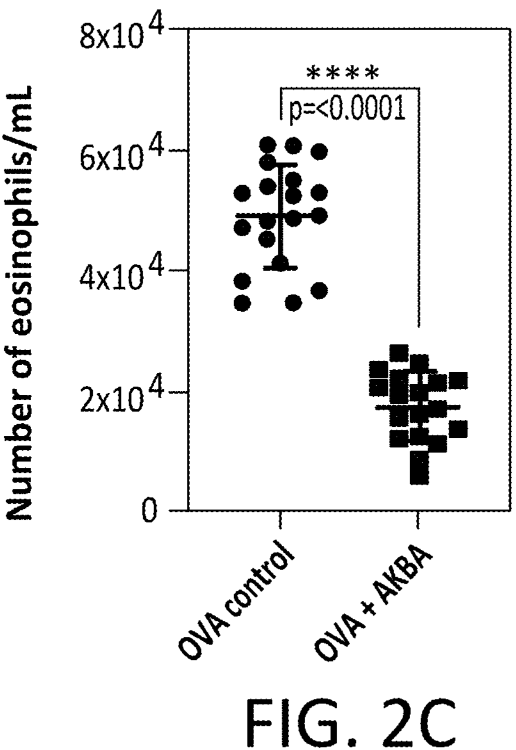
FIG. 2C shows the results when total eosinophil was calculated representing mean±SD (OVA control and OVA+AKBA n=20).
Figure 2D:
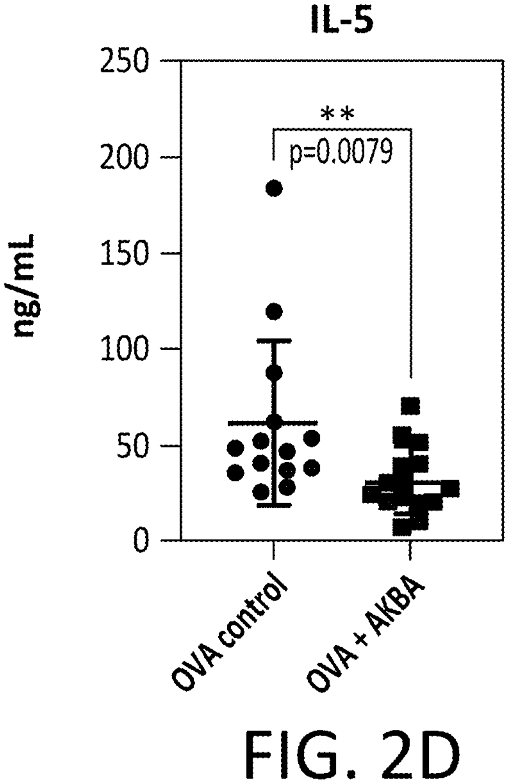
FIGS. 2D, 2E, 2F, and 2G show results when BAL fluid was analyzed for cytokine makers in both experimental groups of mice (n=14-15). Values represent mean±SD. *Indicates a significant difference between AKBA-treated mice vs OVA control ($p=0.05$.
Figure 2E:
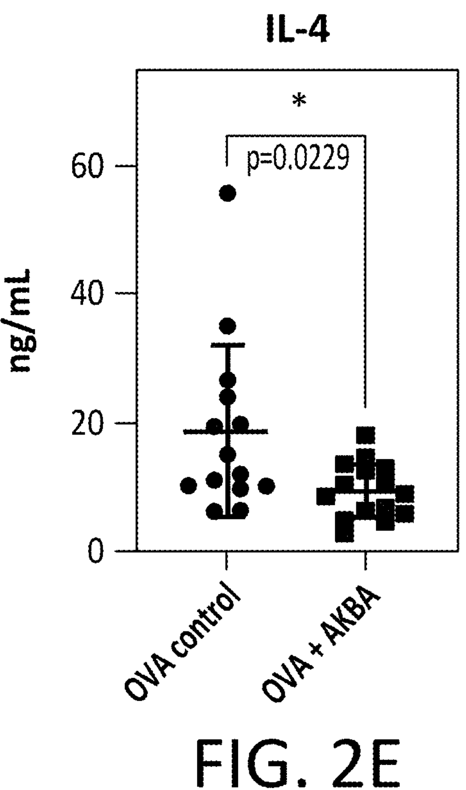
Figure 2F:
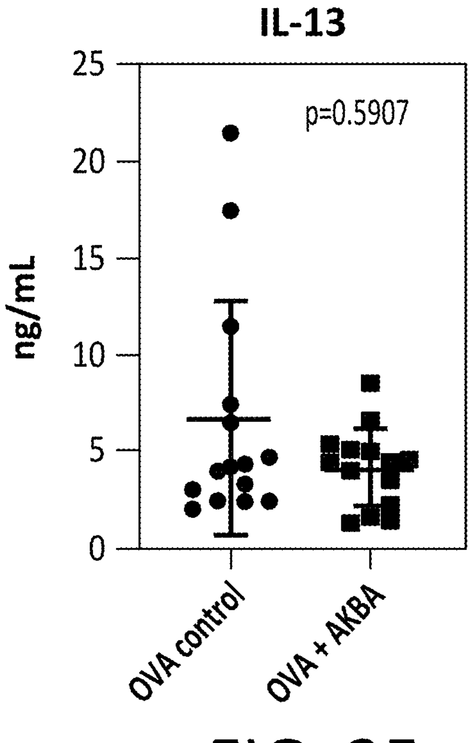
Figure 2G:
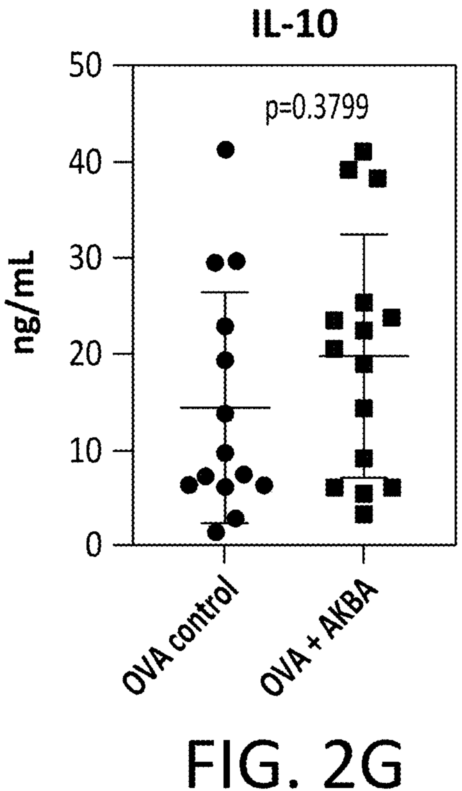

Cell type in BAL also differed between the 3 groups. Both OVA sensitized groups of mice (OVA control and OVA+AKBA) showed a significant increase in airway eosinophilia when compared to naïve mice. Percent eosinophil was lower in OVA+AKBA groups, having 31.4% eosinophil percentage compared to the 48.9% concentration the OVA control group displayed (FIG. 2B). As expected, no eosinophils were found in the naïve group. Absolute number of eosinophils/ml showed mice from the OVA control group had significantly higher counts (48934.39±8321.83 eosinophil/mL) when compared to the AKBA group (17317.95±5552.67 eosinophil/mL) (FIG. 2C).

Four cytokine markers were measured using flow cytometry of the BAL fluid in both OVA control and OVA+AKBA groups (FIGS. 2D to 2G). The OVA+AKBA groups showed significant lower levels of classic asthma markers IL-5 (FIG. 2D; 62.53±43.62 ng/mL vs 31.39±17.71 ng/mL, Mann-Whitney test, p=0.0079) and IL-4 (FIG. 2E; 18.72±14.72 ng/mL vs 9.30±6.67 ng/mL, Mann-Whitney test, p=0.0229) when compared to the OVA control group. No significant difference was found between the groups when observing IL-13 (FIG. 2F; 6.81±6.15 ng/mL vs 4.15±3.15 ng/mL) or IL-10 (FIG. 2G; 14.54±11.61 ng/mL vs 19.77±12.19 ng/mL). However, trends are seen, with a decrease in IL-13 and increase in IL-10 (anti-inflammatory) for OVA+AKBA groups.

Figure 2H:
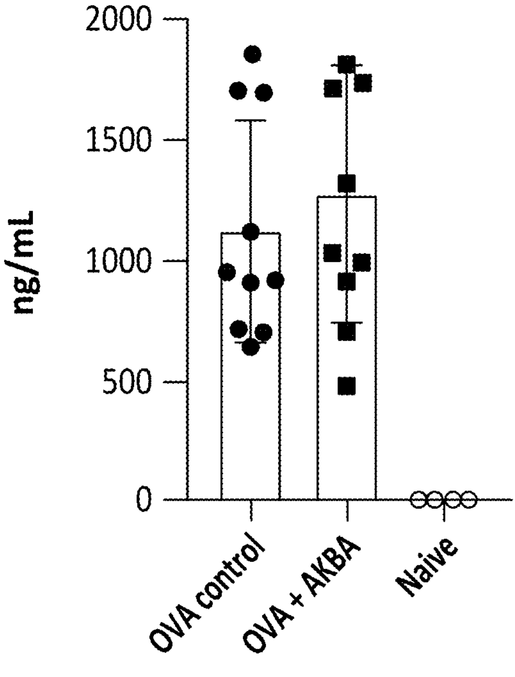
FIG. 2H shows results when Serum was taken at sacrifice for assessment of OVA-specific IgE using anti-OVA ELISA. OVA control and OVA+AKBA (n=15) values represent mean±SD. Naïve animals (n=4) are represented by the dotted line. Indications of significant difference include  as $p=0.05$, * as $p=0.001$ and **** as $p=<0.0001$.

Allergen-specific serum IgE is a hallmark of allergic asthma and allergic airway disease. As such, serum OVA-specific IgE appeared following OVA exposure, with non-detectable levels in naïve animals (FIG. 2H). However, no difference was found between OVA control and OVA+AKBA groups of mice (1120.71±433.94 ng/mL vs 1275.98±503.22 ng/mL Mann-Whitney test, p=0.3223).

Figure 3A:
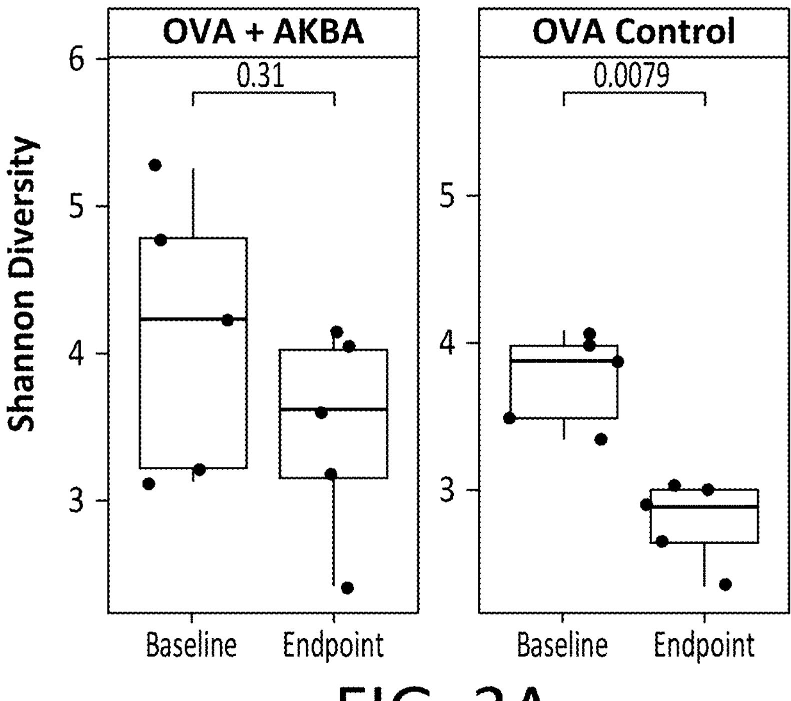
FIGS. 3A-3D show Alpha diversity that was determined for OVA control and OVA+AKBA mice using Shannon and Richness metrics.
Figure 3B:
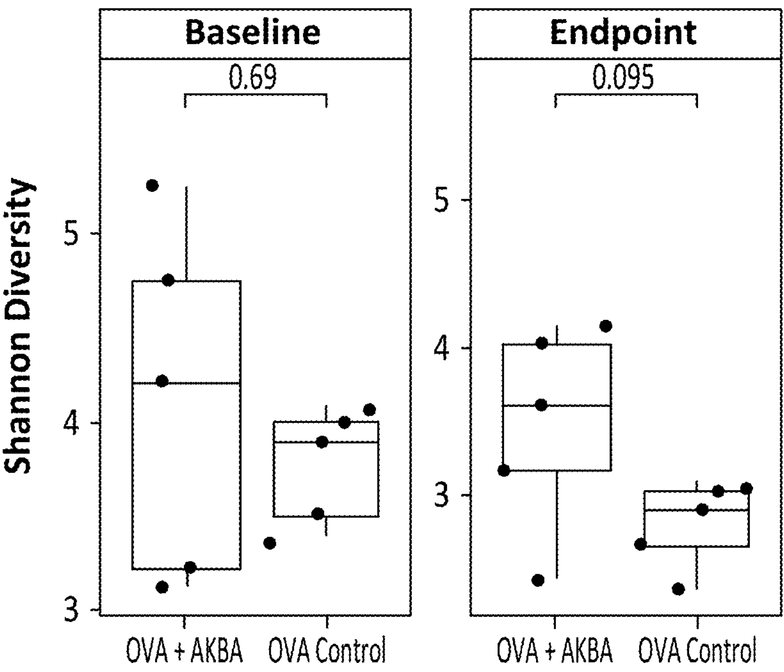
Figure 3C:
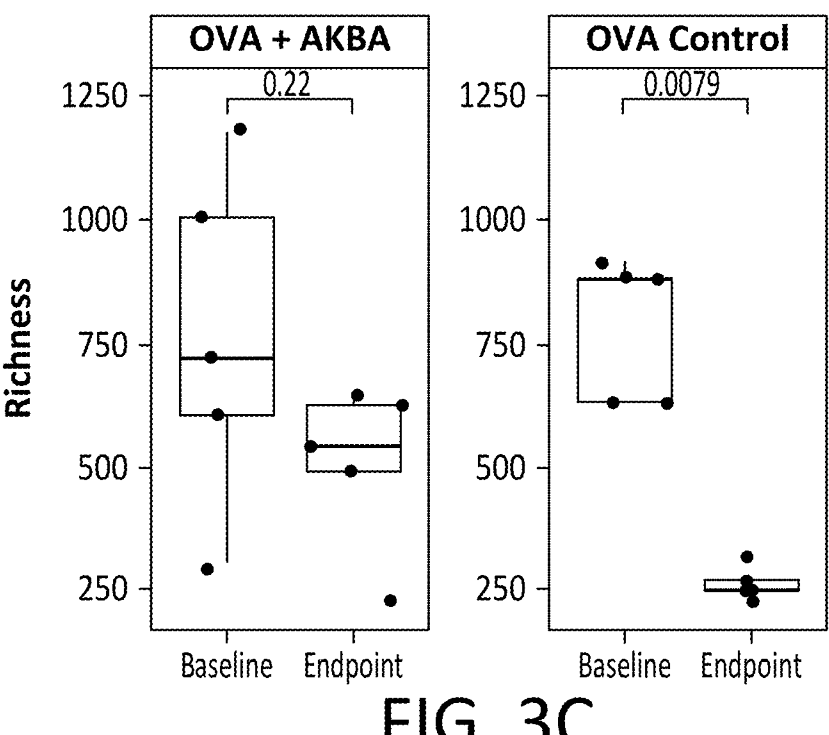
Figure 3D:
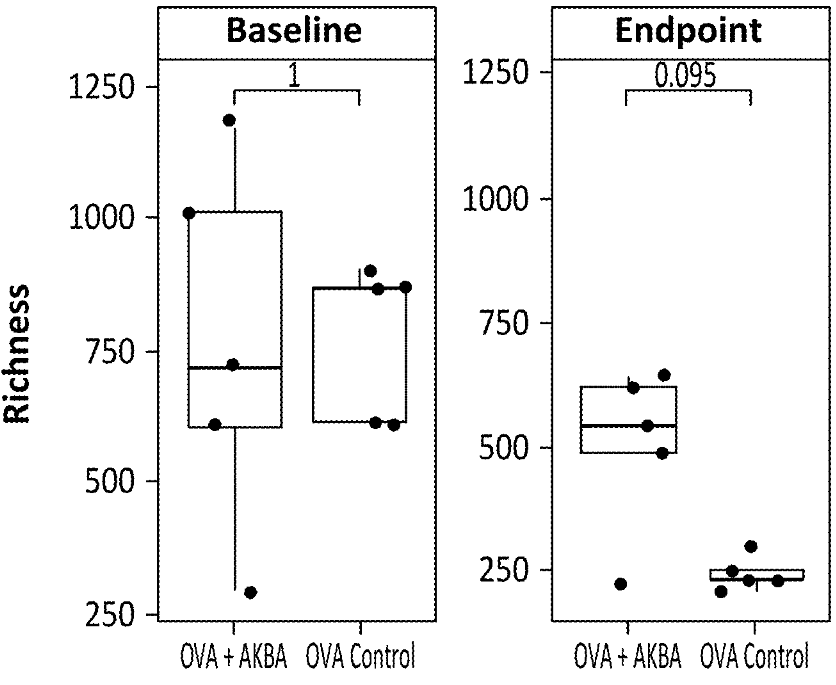
Figure 3E:
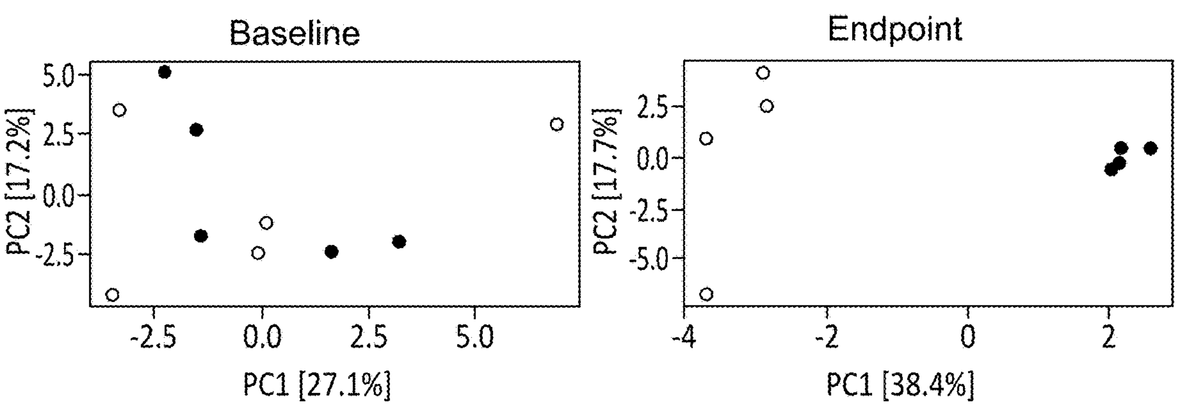
FIG. 3E is PCA plots by analysis of PC1 and PC2 showing disgustable clustering for both OVA+AKBA and OVA control mice at endpoint.

AKBA Supplement Inhibits Loss of Microbiome Diversity in OVA Induced Allergic Airway Model A total number of 4,604,531 high-quality reads were obtained for an average of 68,724 reads per sample. Reads were clustered into 16,920 unique ASV. There was a significant decrease in the Richness measure of alpha diversity (p=0.0079) and Shannon diversity (p=0.0079) from OVA control mice when compared between baseline and endpoint (FIGS. 3A and 3B), suggesting the allergic asthma model is associated with dysbiosis of the gut microbiome. Twenty-four different genera were found significantly decreased in OVA control mice between baseline and end point (DESeq, p<0.05) (Table 1). None of these bacteria were decreased in the OVA+AKBA group. As such, the OVA+AKBA group maintained its overall richness and Shannon diversity from baseline to the endpoint (FIG. 3A, 3B). No significant difference was found between the groups at the same time point; However, OVA+AKBA group had a trend of higher diversity than OVA control group (p=0.095) at the endpoint (FIGS. 3C and 3D). Both OVA and OVA+AKBA were distinguishable by analysis of PC1 and PC2 at endpoint (FIG. 3E). No difference was found between baseline microbiomes for both groups for diversity and baseline bacterial composition.

TABLE 1

Genera decreased in OVA control mice between baseline and end point

| Genus | log2FC | lfcSE | Pvalues | FDR |
|---|---|---|---|---|
| *Candidatus_ Branchiomonas* | −23.586 | 3.0264 | 6.52E−15 | 2.61E−13 |
| *Ellin6055* | −7.9377 | 1.1098 | 8.52E−13 | 2.27E−11 |
| *Piscinibacter* | −7.3074 | 1.0546 | 4.23E−12 | 8.46E−11 |
| *Devosia* | −6.6326 | 1.045 | 2.20E−10 | 3.52E−09 |
| *Blastococcus* | −7.1679 | 1.1463 | 4.02E−10 | 5.36E−09 |
| *Erysipelatoclostridium* | −7.3174 | 1.2428 | 3.91E−09 | 4.46E−08 |
| *Microvirga* | −6.88 | 1.6374 | 2.65E−05 | 0.000163 |
| *Pseudonocardia* | −6.3668 | 1.6469 | 0.000111 | 0.000632 |
| *Ramlibacter* | −6.0478 | 1.6324 | 0.000211 | 0.001057 |
| *Candidatus_ Udaeobacter* | −6.6494 | 1.8521 | 0.000331 | 0.001469 |
| *Arenimonas* | −6.1188 | 1.7206 | 0.000376 | 0.001544 |
| *Bradyrhizobium* | −6.0307 | 1.7483 | 0.000562 | 0.00214 |
| *Massilia* | −5.2897 | 1.5629 | 0.000713 | 0.002594 |
| *Pseudarthrobacter* | −3.9528 | 1.2151 | 0.001141 | 0.003969 |
| *Aridibacter* | −5.5249 | 1.7285 | 0.001392 | 0.004639 |
| *Ochrobactrum* | −4.7177 | 1.4981 | 0.001637 | 0.005239 |
| *Citricoccus* | −6.7466 | 2.2666 | 0.002916 | 0.008751 |
| *Thermomonas* | −6.0602 | 2.2753 | 0.007733 | 0.021742 |
| *Lachnospiraceae_* UCG_010 | −3.9687 | 1.4936 | 0.007882 | 0.021742 |
| *Puia* | −5.8719 | 2.3057 | 0.010876 | 0.028066 |
| RB41 | −5.6721 | 2.3225 | 0.014599 | 0.036497 |
| *Corallococcus* | −5.6448 | 2.3651 | 0.017002 | 0.040382 |
| *Akkermansia* | −1.8733 | 0.78605 | 0.017162 | 0.040382 |
| *Rubrobacter* | −5.3954 | 2.3691 | 0.02276 | 0.049211 |

Dietary AKBA Supplement Significantly Increases Relative Abundances of *Bifidobacterium*

Figure 3F:
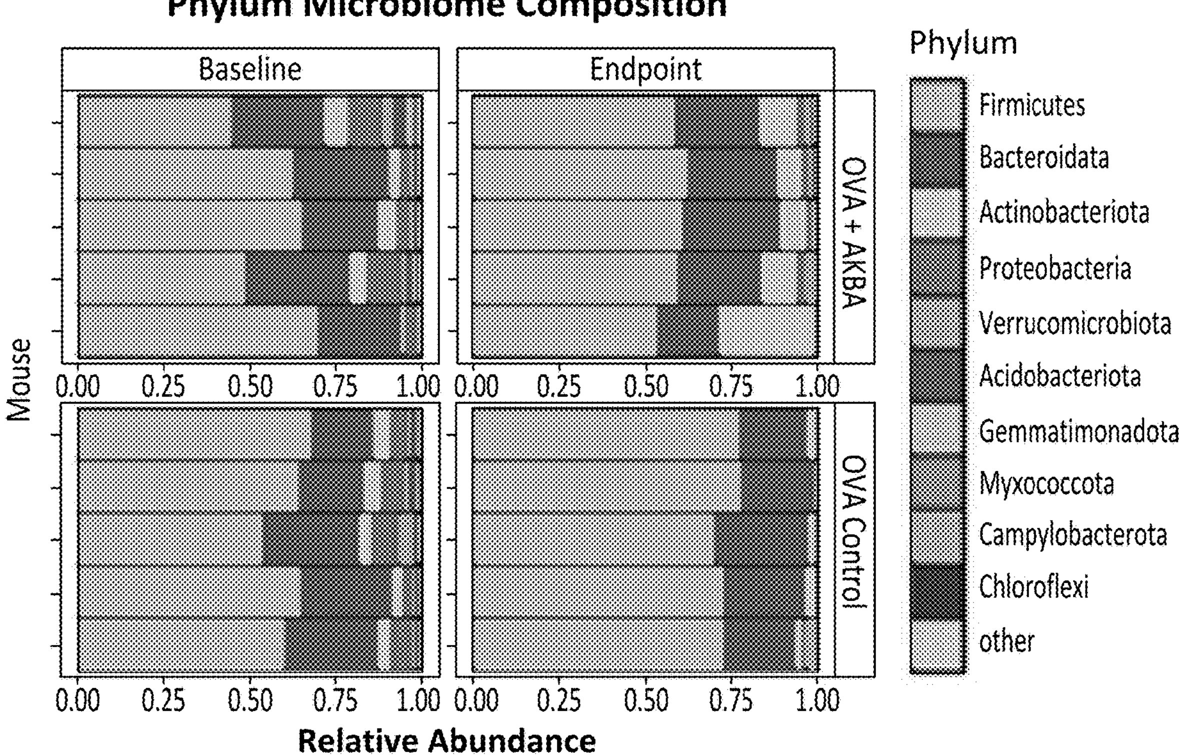
FIG. 3F is a Bar plot showing relative abundance changes between baseline, endpoint, OVA control and OVA+AKBA for phylum.

A difference was observed between baseline and endpoint at both phylum and genus level for the OVA control group of mice (FIG. 3F). At the phylum level, Proteobacteria was found significantly diminished, along with Verrucomicrobia and Actinobacteria in OVA control mice. However, Firmicutes and *Lactobacillus* were found significantly increased (DESeq, $p<0.05$). Interestingly, a significantly higher relative abundances of Actinobacteria phyla and *Bifidobacterium* genus was found in OVA+AKBA vs OVA control mice (FIG. 3F). *Bifidobacterium* increased by a 15.94±15.84-fold change in the OVA+AKBA while only increasing by a 0.75±1.27-fold change in the OVA control (Wilcoxon test p=0.07). Other six bacteria, with relatively lower abundances than *Bifidobacterium*, were also significantly changed in AKBA treated mice between baseline and endpoint, including increases in Lactiplantibacillus, Lacticaseibacillus and *Turicibacter*, along with decreases in *Hyphomicrobium, Solirubrobacter* and *Steroidobacter* (DESeq, $p<0.05$).

*Bifidobacterium* ASV was Identified as *Bifidobacterium pseudolongum*

Figure 5A:
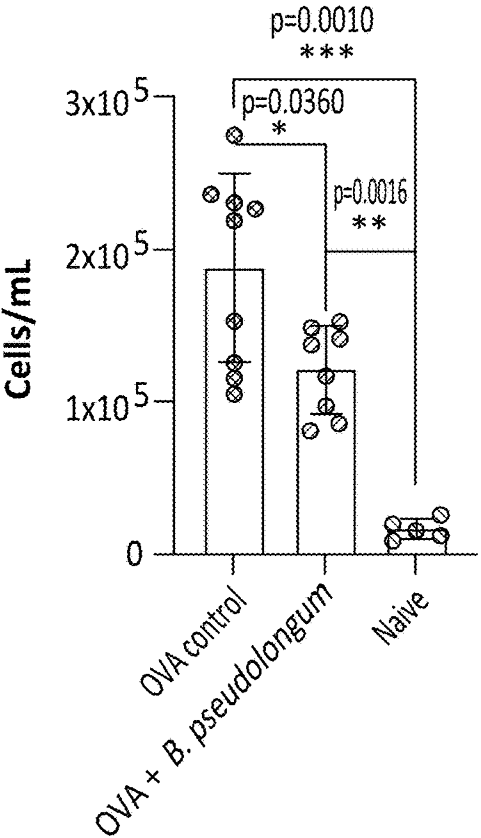
FIG. 5A shows the results when the BAL fluid was analyzed for total cell number in three groups of mice. The analysis was performed as follows: mice that were sensitized and challenged with ova (column 1) (n=10); mice that were sensitized and challenged with ova and treated with *B. pseudolongum* (column 2) (n=10); naive mice (column 3) (n=5); Values represent mean±SD.
Figure 5B:
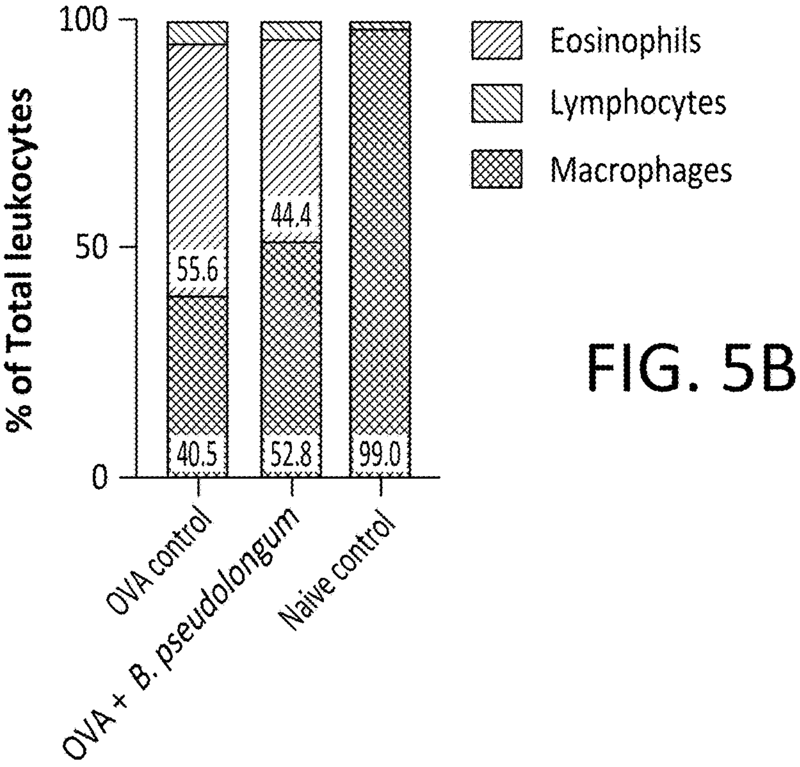
FIG. 5B shows that the Cell differentiation were counted and based on percentage.

Only one *Bifidobacterium* ASV was shown to increase in our experiments. To further identify the taxonomy of this *Bifidobacterium* ASV, all 5 OVA+AKBA stool pellets were combined at the endpoint, and 15 random *Bifidobacterium* colonies were isolated using *Bifidobacterium* selective media. All 15 bacterial samples were identical, and the ITS sequences are most closely related to *Bifidobacterium pseudolongum* strain UMB-MBP-01 in NCBI nucleotide database with accession number CP022544.1 (98.92% identity). To explore whether *B. pseudolongum* has mediated protection of asthma in AKBA treated mice, the allergic airway model was repeated with oral gavages of $10^8$ CFU *B. pseudolongum* (FIG. 5B).

Figure 4A:
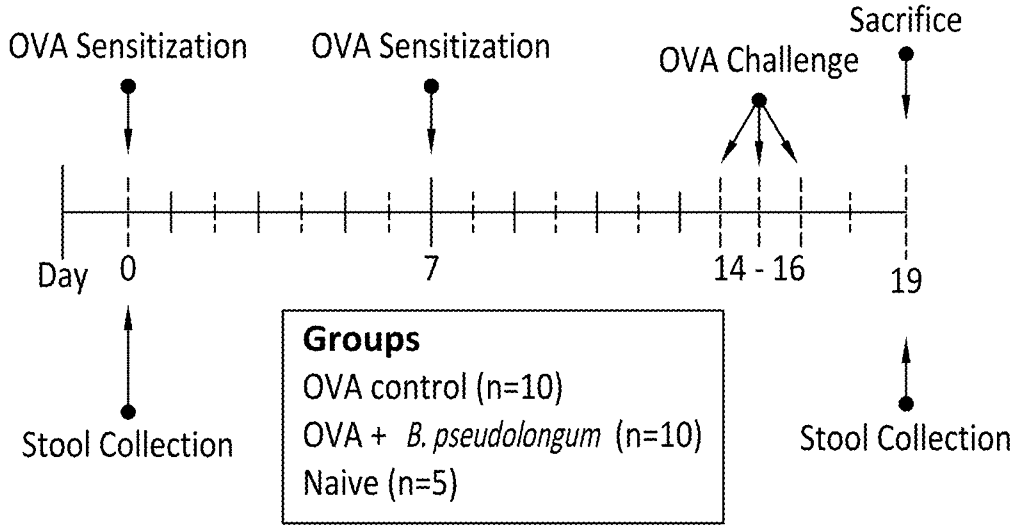
FIG. 4A shows an induction of allergic airway model, *B. pseudolongum* supplementation course and average weight (g) of mice and percent change following the duration of experiment. Colored lines corresponding to $1\times10^8$ *B. pseudolongum* oral supplementation. Values in each column which have different letters are significantly different ($p<0.05$). (n=10 for experimental groups, n=5 for naïve group).

*B. pseudolongum* Attenuated Ovalbumin-Dependent Allergic Airway Inflammation with Decreased Concentrations of Inflammation Markers As AKBA supplementation was found to significantly decrease body weight in mice, *B. pseudolongum* treated mice were examined to see if they captured a similar phenotype (FIG. 4A). Indeed, mice given *B. pseudolongum* were found to gain weight significantly slower than both the OVA control and naïve group of mice (unpaired t-test, p=0.013, p=0.007). No weight change or percent change was seen between the OVA control and naïve group (unpaired t-test p=0.75).

Next, airway inflammations in *B. pseudolongum* treated mice was measured, as it was done in the AKBA experiment. The OVA control group of mice had 92.2% (Mann-Whitney test, p=0.0010) more leukocyte counts than the naïve group. The *B. pseudolongum* group also had significantly higher counts than the naïve control, by 87.0% (Mann-Whitney test, p=0.0016). However, total leukocyte counts were significantly lower in those given *B. pseudolongum* versus the OVA control group by 36.1% (Mann-Whitney test, p=0.036) (FIG. 5A).

Figure 5C:
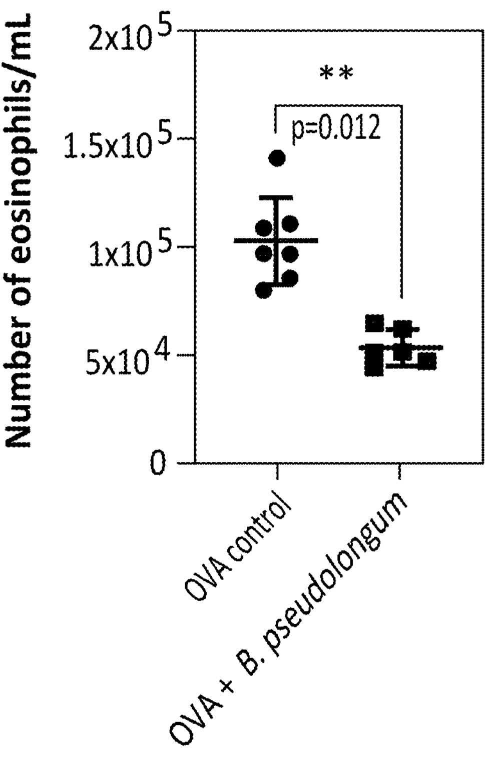
FIG. 5C shows that the total eosinophil was calculated representing mean±SD.
Figure 6A:
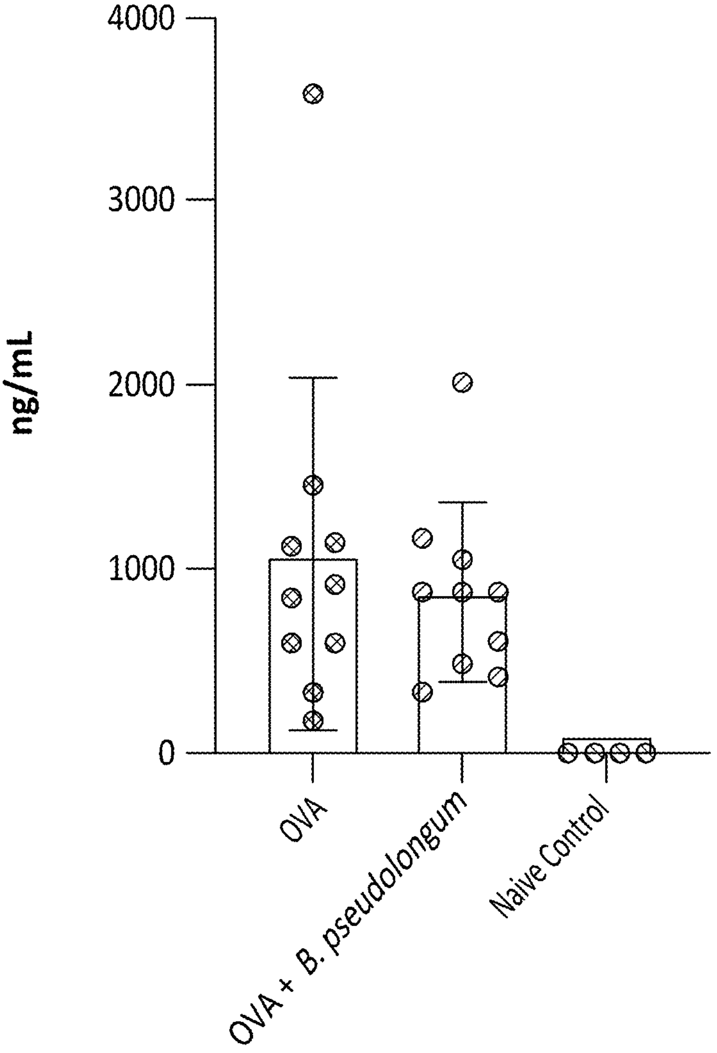
FIG. 6A shows that *B. pseudolongum* does not affect ovalbumin-blood IgE levels in allergic airway inflammation. Serum was taken at sacrifice for assessment of OVA-specific IgE using anti-OVA ELISA. OVA and OVA+*B. pseudolongum* (n=10) values represent mean±SD. Naïve animals (n=5) are represented by the dotted line. *Significant difference is only shown between naïve groups and OVA treated groups.

Cell type also differed between the 3 groups. OVA challenged mice showed a significant increase in airway eosinophilia when compared to naïve mice (75311.21±16642.62 cells/mL vs 0 cells/mL). Percent eosinophil was lower in OVA+*B. pseudolongum* groups (62381.80±8869.84 cells/mL), having 44.6% eosinophil percentage compared to the 55.0% concentration the OVA control group displayed (FIGS. 5B and 5C). As expected, no eosinophils were found in the naïve group. *B. pseudolongum* did not affect ovalbumin-blood IgE levels (FIG. 6A).

Figure 5D:
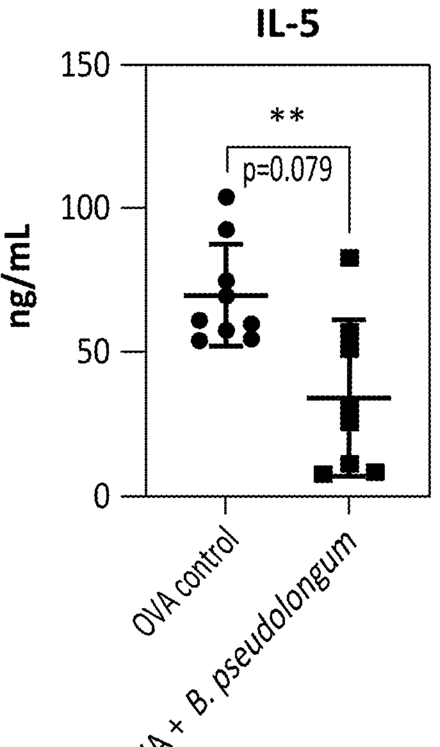
FIGS. 5D-5G show the data when the BAL fluid was analyzed for cytokine markers in both experimental groups of mice (OVA n=10, OVA+*B. pseudolongum* n=8). Values represent mean±SD. Indications of significant difference include  as p=0.05, * as p=0.001 and **** as p=<0.0001.
Figure 5E:
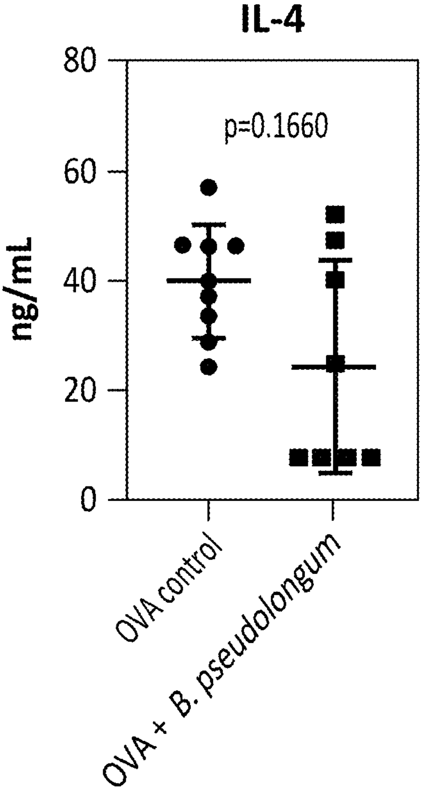
Figure 5F:
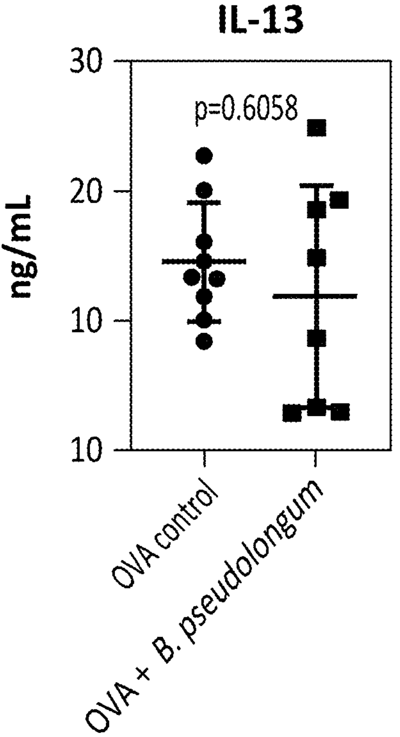
Figure 5G:
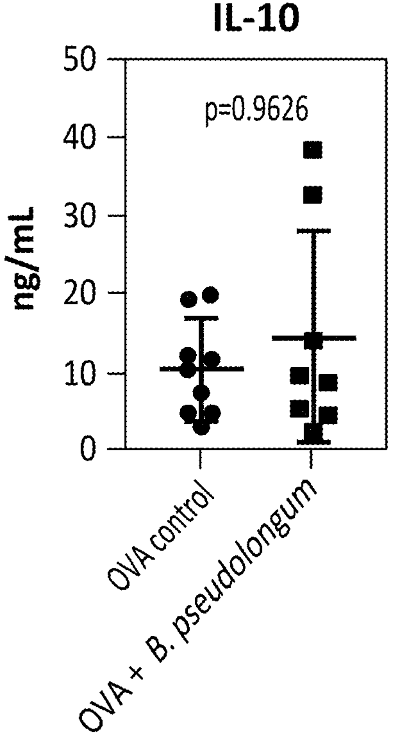

Four cytokine markers were measured using flow cytometry of the BAL fluid in both OVA control and OVA+*B. pseudolongum* groups (FIGS. 5D and 5G). The OVA+*B. pseudolongum* group showed significant lower levels of IL-5 (69.50±16.67 ng/mL vs 34.03±25.24 ng/mL, Mann-Whitney test, p=0.0079) when compared to the OVA control group. No significant difference was found between the groups when observing IL-4 (40.08±9.70 ng/mL vs 24.40±18.24 ng/mL) IL-13 (14.05±4.30 ng/mL vs 11.88±8.00 ng/mL) or IL-10 (10.37±5.82 ng/mL vs 14.43±12.70 ng/mL). However, encouraging trends are seen, with a decrease in IL-4 and IL-13 and increases in IL-10 (anti-inflammatory) for OVA+*B. pseudolongum.*

Successful Colonization of *B. pseudolongum* and its Impact on Other Microbial Compositions To determine colonization status of *B. pseudolongum*, the gut microbiome was profiled before and after treatment in OVA+*B. pseudolongum* and OVA control groups. The OVA control group had a significant decrease in Shannon diversity between baseline and endpoint (Wilcoxon, p=0.015). By contrast, bacterial diversity maintained a similar level from baseline to endpoint in the OVA+*B. pseudolongum* group (p=0.35). This result recapitulated findings in the AKBA oral supplementation experiment.

Figure 4B:
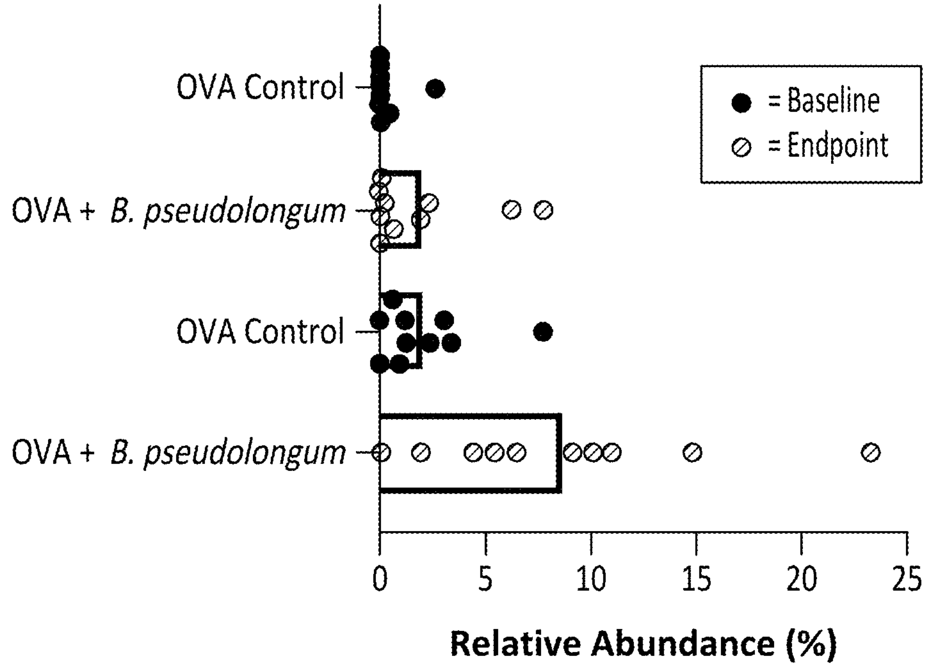
FIG. 4B shows a percent relative abundance of *B. pseudolongum* at both baseline and endpoints. Ova+*B. pseudolongum* were given $1\times10^8$ *B. pseudolongum* supplementation according to experimental design.

As expected, the top taxa at the phylum and genus showed a higher relative abundance of Actinobacteria phyla and *Bifidobacterium* genus in OVA+*B. pseudolongum* vs OVA control mice at the end of the experiment (DESeq $p<0.05$). There was an average of 0.31±0.75% and 2.04±2.21% relative abundance in the starting OVA and OVA+*B. pseudolongum* mice, respectfully. At the end of the experiment, there was 1.91±2.67% and 8.66±6.40% relative abundance found within the gut (FIG. 4B). This data suggests that Oral gavages of *B. pseudolongum* colonized successfully in the guts of the OVA+*B. pseudolongum* group of mice.

Figure 6B:
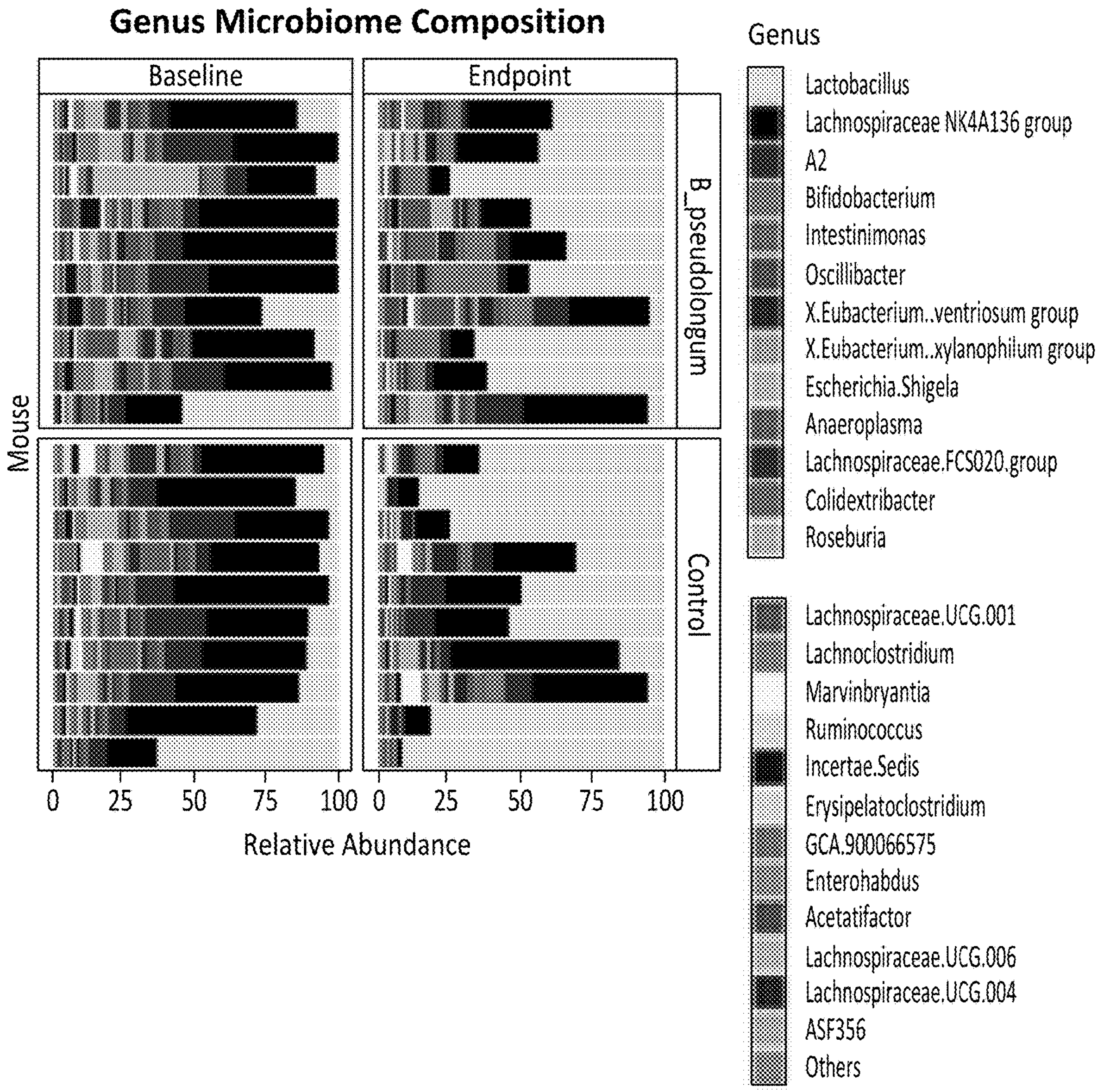
FIG. 6B is a Bar plot of genus level differences between baseline and endpoint of OVA control and OVA+*B. pseudolongum* groups.

To test whether colonization of *B. pseudolongum* affected other bacterial compositions, a comparison between baseline and endpoints compositions was performed. Both groups shared changes in microbiota, including increases in the genus *Lactobacillus, Eubacterium* ventriosum and decreases in Oscillibacter (DESeq $p>0.05$). The Erysipelatoclostridium genus was found increased only in the OVA+*B. pseudolongum* group (FIG. 6B). No differences in bacterial abundance or diversity were found between OVA control and OVA+*B. pseudolongum* at baseline.

Discussion

A water-soluble dietary form of frankincense (AKBA) was shown to help alleviate and potentially protect against, allergic asthma in mice. As mentioned, AKBA is thought to improve inflammatory diseases through a variety of different mechanisms. Here, a new pathway involving the modulation of the gut microbiome, with increases in *B. pseudolongum*, is proposed to help decrease allergic asthma inflammation.

It is not uncommon to see a loss of diversity in both asthma animal models and asthmatic patients. Loss of gut microbiome diversity is thought to be related to, or the cause of, inflammatory diseases. However, dietary AKBA was shown to keep the supplemented animals from loss of gut microbiome diversity while increases probiotic-like bacteria such as Lactiplantibacillus, Lacticaseibacillus and anti-inflammatory related bacteria like *Bifidobacterium* [15]. *Bifidobacterium* and Lactiplantibacillus levels in the gut have been reported to be inversely correlated with inflammation in disease models. Our findings suggest the consideration of AKBA as a prebiotics to facilitate asthma treatment.

Certain bacterial genera associated with anti-inflammatory effects (including *Lactobacillus* and *Bifidobacterium*) are thought to regulate Th2 inflammatory cells and prevent allergies by lowering IgE levels. Our data did not find a change in blood IgE levels following AKBA or *B. pseudolongum* supplementation. However, as asthma is a lung disease, differences in IgE levels may be observed in the lungs as opposed to systemically.

*Bifidobacterium* is a known probiotic bacteria and has been used in asthma studies before for its anti-allergy effects. Many of these studies look at specifically *B. infantis*, an important infant gut bacteria. In this study, however, an increase in *B. pseudolongum* was seen. This bacteria is mainly found in the guts of animals with fur (calves, piglets, chickens, dogs, and others). However, it is only found in small numbers in humans. To date, *B. pseudolongum* has not been widely discussed in human health. Interestingly, decreases in allergic disease are thought to be linked to animal ownership (cat, dog, farm animals). The protective effect of animals may include an increase in microbial diversity. Very importantly, *B. pseudolongum* has been found to be increased in the gut of children who have continuous interaction with an animal. *B. pseudolongum* has a protective effect on alleviating airway inflammation in asthma. More research should be conducted on the protective nature of *B. pseudolongum* and its linkage to animal exposure and asthma.

Following *B. pseudolongum* supplementation in the second set of experiments, only one genus, Erysipelatoclostridium, was found significantly different from the OVA control group. Erysipelatoclostridium is a Gram-positive anaerobic bacterium that is part of the normal human gut microbiota and is known to cause infections in different parts of the body. However, it has also been found to be a butyrate producing bacteria. Butyrate production in the gut has been associated with major health benefits, including a reduced risk of inflammatory diseases and Treg function. Previous studies have also associated human dairy intake with increases in Erysipelatoclostridium spp [Smith-Brown, P., et al., Dairy and plant based food intakes are associated with altered faecal microbiota in 2 to 3 year old Australian children. Sci. Reports 2016 61 6, 1-8 (2016)]. *Bifidobacterium* is commonly used in dairy fermentation. The connection between the two bacteria should be further explored. It should be noticed, however, that the overall microbiome composition following *B. pseudolongum* supplementation was not significantly different. This leads us to hypothesize that *B. pseudolongum*'s anti-asthma effect is specific to itself and not due to a change in microbiome composition.

An interesting question is what causes the alteration of the gut microbiome upon administration of AKBA in our allergic asthma model. AKBA increases relative abundances of *Bifidobacterium* in healthy mice, and AKBA selectively inhibited certain gut microbiota including *Akkermansia* in vitro, but showed no direct feeding effect on Bifidobacteria. Thus, one possibility is that the increased *Bifidobacterium* is a result of less competition for growth in the gut, as both Bifidobacteria and *Akkermansia* can colonize gut mucosa and use mucin as energy source. Other studies have shown *B. pseudolongum* increased in the gut of mice which survived lethal influenza infections. From this, it was believed that this bacteria may enhance the host influenza resistance when lethal infection occur. However, there is a need to understand the gut microbiomes response to decreases in inflammation and if a state of anti-inflammation can increase certain microbes.

Another interesting finding relates to weight loss in mice given AKBA. It is possible AKBA may increase weight loss potential through microbiome changes. *Bifidobacterium* has been shown to contribute to weight loss in both mice and humans. *B. pseudolongum* supplementation was also found to retard weight gain of the mice. Fasting blood glucose levels were seen decreased in patients given *B. longum*. *B. longum* 's potential to regulate host metabolisms or insulin resistance should be explored. It would be of interest to test the effect of AKBA or *B. pseudolongum* supplementation on obesity related asthma.

Of interest, *B. pseudolongum* should be investigated as a new human probiotic and fermentation starter. *Bifidobacterium animalis* subsp. *lactis* is commonly used in fermented food products for its flavor characteristics and health effects. As *B. pseudolongum* is animal derived, different characteristics may occur when used with animal dairy products. Additionally, the stability of AKBA in a variety of food products should be explored.

A small human trial, of a daily 500 mg dose of a combination of boswellic acids, showed a decrease in inhalation therapy for asthmatic patients [Ferrara, T., et al., Functional study on *Boswellia* phytosome as complementary intervention in asthmatic patients. Eur. Rev. Med. Pharmacol. Sci. 19, 3757-3762 (2015)]. A more recent clinical trial has shown 1:1 ratio of extracts of *Boswellia serrata* gum resin and *Aegle marmelos* fruit containing 30 mg AKBA to decrease overall asthma scores and serum IL-4, and increase IFN-γ compared to a placebo group [Yugandhar, P., et al., A novel herbal composition containing extracts of *Boswellia serrata* gum resin and *Aegle marmelos* fruit alleviates symptoms of asthma in a placebo controlled double-blind clinical study. *Phyther. Res.* 32, 140-150 (2018)]. However, no microbiome study has been conducted. Famously, translation from animal study to humans can have problems. As AKBA has been shown to lessen asthma and arthritis in humans, it is a good candidate to investigate further into AKBA-human gut microbiome interactions. AKBA's effect on the gut microbiome following different allergic diseases should be investigated for similar results.

Oral AKBA was shown to attenuate airway inflammation and improve airway hyperresponsiveness. This effect, at least partially, may be mediated by increases of a specific bacterial species that is commonly found in pets, farm animals and other fur animals. The beneficial effects of AKBA on the gut are still largely undiscovered and may prove to be an important supplement to human health. Future aspects of AKBA and *B. pseudolongum* as a functional ingredients should be explored.

The study was conducted according to the guidelines of the Declaration of Helsinki, and approved by the Institutional Review Board of University of Connecticut Health protocol 102063-0522 as of 30 Aug. 2019.

Definitions

Compounds and materials are described using standard nomenclature. Unless defined otherwise, all technical and scientific terms used herein have the same meaning as is commonly understood by one of skill in the art to which this invention belongs. The following terms are used to describe the invention of the present disclosure. In instances where a term is not specifically defined herein, that term is given an art-recognized meaning by those of ordinary skill applying that term in context to its use in describing the present disclosure.

The use of the terms "a" and "an" and "the" and similar referents (especially in the context of the following claims) are to be construed to cover both the singular and the plural, unless otherwise indicated herein or clearly contradicted by context. By way of example, "an element" means one element or more than one element.

It should also be understood that, in certain methods described herein that include more than one step or act, the order of the steps or acts of the method is not necessarily limited to the order in which the steps or acts of the method are recited unless the context indicates otherwise. Furthermore, the terms first, second, etc., as used herein are not meant to denote any particular ordering, but simply for convenience to denote a plurality of, for example, layers.

The terms “comprising”, “having”, “including”, and “containing” are to be construed as open-ended terms (i.e., meaning “including, but not limited to”) unless otherwise noted.

The terms “about” or “approximately,” as used herein, is inclusive of the stated value and means within an acceptable range of deviation for the particular value as determined by one of ordinary skill in the art, considering the measurement in question and the error associated with measurement of the particular quantity (i.e., the limitations of the measurement system). For example, “about” can mean within one or more standard deviations, or within ±10% or 5% of the stated value. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., “such as”), is intended merely to better illustrate the invention and does not pose a limitation on the scope of the invention unless otherwise claimed. No language in the specification should be construed as indicating any non-claimed element as essential to the practice of the invention as used herein.

The phrase “and/or,” as used herein in the specification and in the claims, should be understood to mean “either or both” of the elements so conjoined, i.e., elements that are conjunctively present in some cases and disjunctively present in other cases. Multiple elements listed with “and/or” should be construed in the same fashion, i.e., “one or more” of the elements so conjoined. Other elements may optionally be present other than the elements specifically identified by the “and/or” clause, whether related or unrelated to those elements specifically identified. Thus, as a non-limiting example, a reference to “A and/or B”, when used in conjunction with open-ended language such as “comprising” can refer, in one embodiment, to A only (optionally including elements other than B); in another embodiment, to B only (optionally including elements other than A); in yet another embodiment, to both A and B (optionally including other elements); etc.

As used herein in the specification and in the claims, “or” should be understood to have the same meaning as “and/or” as defined above. For example, when separating items in a list, “or” or “and/or” shall be interpreted as being inclusive, i.e., the inclusion of at least one, but also including more than one, of a number or list of elements, and, optionally, additional unlisted items. Only terms clearly indicated to the contrary, such as “only one of” or “exactly one of,” or, when used in the claims, “consisting of,” will refer to the inclusion of exactly one element of a number or list of elements. In general, the term “or” as used herein shall only be interpreted as indicating exclusive alternatives (i.e., “one or the other but not both”) when preceded by terms of exclusivity, such as “either,” “one of,” “only one of,” or “exactly one of.”

As used herein in the specification and in the claims, the phrase “at least one,” in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase “at least one” refers, whether related or unrelated to those elements specifically identified. Thus, as a nonlimiting example, “at least one of A and B” (or, equivalently, “at least one of A or B,” or, equivalently “at least one of A and/or B”) can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase “one or more,” as used herein, means at least one, and thus includes individual components as well as mixtures/combinations of the listed components in any combination.

Other than in the operating examples, or where otherwise indicated, all numbers expressing quantities of ingredients and/or reaction conditions are to be understood as being modified in all instances by the term “about,” meaning within 10% of the indicated number (e.g., “about 10%” means 9%-11% and “about 2%” means 1.8%-2.2%).

All percentages and ratios are calculated by weight unless otherwise indicated. All percentages are calculated based on the total composition unless otherwise indicated. Generally, unless otherwise expressly stated herein, “weight” or “amount” as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

All ranges and amounts given herein are intended to include subranges and amounts using any disclosed point as an end point. Thus, a range of “1% to 10%, such as 2% to 8%, such as 3% to 5%,” is intended to encompass ranges of “1% to 8%,” “1% to 5%,” “2% to 10%,” and so on. All numbers, amounts, ranges, etc., are intended to be modified by the term “about,” whether or not so expressly stated. Similarly, a range given of “about 1% to 10%” is intended to have the term “about” modifying both the 1% and the 10% endpoints. Further, it is understood that when an amount of a component is given, it is intended to signify the amount of the active material unless otherwise specifically stated.

As used herein, the term “administering” means the actual physical introduction of a composition into or onto (as appropriate) a subject, a host or cell. Any and all methods of introducing the composition into the subject, host or cell are contemplated according to the invention; the method is not dependent on any particular means of introduction and is not to be so construed. Means of introduction are well-known to those skilled in the art, and also are exemplified herein.

As used herein, "optional" or "optionally" means that the subsequently described event or circumstance may or may not occur, and that the description includes instances where said event or circumstance occurs and instances where it does not.

As used herein, the term "pharmaceutically acceptable" refers to compositions that are physiologically tolerable and do not typically produce an allergic or similar untoward reaction when administered to a subject, preferably a human subject. Preferably, as used herein, the term "pharmaceutically acceptable" means approved by a regulatory agency of a federal or state government or listed in the U.S. Pharmacopeia or other generally recognized pharmacopeia for use in animals, and more particularly in humans.

As used herein, the terms "treat," "treating," and "treatment" include inhibiting the pathological condition, disorder, or disease, e.g., arresting or reducing the development of the pathological condition, disorder, or disease or its clinical symptoms; or relieving the pathological condition, disorder, or disease, e.g., causing regression of the pathological condition, disorder, or disease or its clinical symptoms. These terms also encompass therapy and cure. Treatment means any way the symptoms of a pathological condition, disorder, or disease are ameliorated or otherwise beneficially altered. Preferably, the subject in need of such treatment is a mammal, preferably a human.

As used herein, the term "effective amount" refers to the amount of a therapy, which is sufficient to reduce or ameliorate the severity and/or duration of a disorder or one or more symptoms thereof, inhibit or prevent the advancement of a disorder, cause regression of a disorder, inhibit or prevent the recurrence, development, onset or progression of one or more symptoms associated with a disorder, detect a disorder, or enhance or improve the prophylactic or therapeutic effect(s) of another therapy (e.g., prophylactic or therapeutic agent). An effective amount can require more than one dose.

Effective amounts may vary depending upon the biological effect desired in the individual, condition to be treated, and/or the specific characteristics of the composition according to the present invention and the individual. In this respect, any suitable dose of the composition can be administered to the patient (e.g., human), according to the type of disease to be treated. Various general considerations taken into account in determining the "effective amount" are known to those of skill in the art and are described, e.g., in Gilman et al., eds., Goodman And Gilman's: *The Pharmacological Bases of Therapeutics,* 8th ed., Pergamon Press, 1990; and Remington's Pharmaceutical Sciences, 17th Ed., Mack Publishing Co., Easton, Pa., 1990, each of which is herein incorporated by reference. The dose of the composition according to the present invention desirably comprises about 0.1 mg per kilogram (kg) of the body weight of the patient (mg/kg) to about 400 mg/kg (e.g., about 0.75 mg/kg, about 5 mg/kg, about 30 mg/kg, about 75 mg/kg, about 100 mg/kg, about 200 mg/kg, or about 300 mg/kg). In another embodiment, the dose of the composition according to the present invention comprises about 0.5 mg/kg to about 300 mg/kg (e.g., about 0.75 mg/kg, about 5 mg/kg, about 50 mg/kg, about 100 mg/kg, or about 200 mg/kg), about 10 mg/kg to about 200 mg/kg (e.g., about 25 mg/kg, about 75 mg/kg, or about 150 mg/kg), or about 50 mg/kg to about 100 mg/kg (e.g., about 60 mg/kg, about 70 mg/kg, or about 90 mg/kg).

The term "subject" is used herein to refer to an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, and a whale), a bird (e.g., a duck or a goose), and a shark. In an embodiment, the subject is a human, such as a human being treated or assessed for a disease, disorder or condition, a human at risk for a disease, disorder or condition, a human having a disease, disorder or condition, and/or human being treated for a disease, disorder or condition as described herein. In some embodiments, the subject does not suffer from an ongoing autoimmune disease. In one embodiment, the subject is about 1, 2, 3, 4, 5, 6, 7, 8, 9, or 10 years of age. In another embodiment, the subject is about 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-100 years of age. Values and ranges intermediate to the above recited ranges are also intended to be part of this invention. In addition, ranges of values using a combination of any of the above-recited values as upper and/or lower limits are intended to be included.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art of this disclosure.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group.

All compounds are understood to include all possible isotopes of atoms occurring in the compounds. Isotopes include those atoms having the same atomic number but different mass numbers and encompass heavy isotopes and radioactive isotopes. By way of general example, and without limitation, isotopes of hydrogen include tritium and deuterium, and isotopes of carbon include $^{11}C$, $^{13}C$, and $^{14}C$. Accordingly, the compounds disclosed herein may include heavy or radioactive isotopes in the structure of the compounds or as substituents attached thereto. Examples of useful heavy or radioactive isotopes include $^{18}F$, $^{15}N$, $^{18}O$, $^{76}Br$, $^{125}I$ and $^{131}I$.

The composition according to the present invention may be administered to a patient by various routes. Examples of routes of administration include, but are not limited to, parenteral, e.g., intravenous, intradermal, subcutaneous, oral, intranasal (e.g., inhalation), transdermal (e.g., topical), transmucosal, and rectal administration. In an embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer.

In accordance with any of the embodiments, the composition according to the present invention can be administered orally to a subject in need thereof. Formulations suitable for oral administration can consist of (a) liquid solutions, such as an effective amount of the compound dissolved in diluents, such as water, saline, or orange juice and include an additive, such as cyclodextrin (e.g., α-, β-, or γ-cyclodextrin, hydroxypropyl cyclodextrin) or polyethylene glycol (e.g., PEG400); (b) capsules, sachets, tablets, lozenges, and troches, each containing a predetermined amount of the active ingredient, as solids or granules; (c) powders; (d) suspensions in an appropriate liquid; and (e) suitable emulsions and gels. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The dose administered to the mammal, particularly human and other mammals, in accordance with the present invention should be sufficient to affect the desired response. One skilled in the art will recognize that dosage will depend upon a variety of factors, including the age, condition or disease state, predisposition to disease, genetic defect or defects, and body weight of the mammal. The size of the dose will also be determined by the route, timing and frequency of administration as well as the existence, nature, and extent of any adverse side-effects that might accompany the administration of a particular composition and the desired effect. It will be appreciated by one of skill in the art that various conditions or disease states may require prolonged treatment involving multiple administrations.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

INCORPORATION BY REFERENCE

All U.S. and PCT patent publications and U.S. patents mentioned herein are hereby incorporated by reference in their entirety as if each individual patent publication or patent was specifically and individually indicated to be incorporated by reference. In case of conflict, the present application, including any definitions herein, will control.

OTHER EMBODIMENTS

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating a patient in need thereof by:

modulating a gut microbiome in the patient, maintaining diversity in the gut microbiome of the patient, and/or increasing a percentage of *Bifidobacterium* in the gut microbiome of the patient;

wherein the method comprises:

administering a composition comprising 3-O-acetyl-11-keto-β-boswellic acid (AKBA) or an extract of *Boswellia serrata* comprising from 30% to 90% AKBA to the patient;

wherein the composition is administered at a dose sufficient to:

increase levels of a first organism in the gut microbiome in comparison to a subject not treated with the composition, wherein the first organism is selected from the group consisting of at least one of:

a. a member of a genus selected from the group consisting of Lactiplantibacillus, Lacticaseibacillus, and *Turicibacter*; and b. *Bifidobacterium pseudolongum*; and decrease levels of a second organism in the gut microbiome in comparison to the subject not treated with the composition, wherein the second organism is selected from the group consisting of at least one member of a genus selected from the group consisting of *Hyphomicrobium, Solirubrobacter* and *Steroidobacter.*

2. The method of claim 1, wherein the method involves maintaining diversity and/or increasing a percentage of *Bifidobacterium* in the gut microbiome of the patient in need thereof, comprising:

administering a composition comprising 3-O-acetyl-11-keto-β-boswellic acid (AKBA) or an extract of *Boswellia serrata* comprising from 30% to 90% AKBA to the patient;

wherein the composition is administered at a dose sufficient to increase the percentage of *Bifidobacterium pseudolongum* in the gut microbiome, compared to a subject not treated with the composition.

3. The method of claim 2, wherein the composition comprises AKBA or the extract of *Boswellia serrata* in combination with a live or lyophilized probiotic bacteria.

4. The method of claim 2, wherein the method further comprises administering a second composition comprising a live or lyophilized probiotic bacteria.

5. The method of claim 1, wherein the method involves increasing a percentage of *Bifidobacterium pseudolongum* in a gut of a patient in need thereof, wherein the method comprises administering the extract of *Boswellia serrata*, wherein the extract of *Boswellia serrata* comprises a therapeutically effective amount of *Boswellia serrata* gum resin comprising boswellic acids.

6. A method of modulating a gut microbiome of a patient comprising:

administering a composition comprising 3-O-acetyl-11-keto-b-boswellic acid (AKBA) or an extract of *Boswellia serrata* comprising from 30-90% AKBA to the patient, wherein the composition is administered at a dose sufficient to:

increase levels of a first organism in the gut microbiome in comparison to a subject not treated with the composition, wherein the first organism is selected from the group consisting of:

a. a member of a genus selected from the group consisting of Lactiplantibacillus, Lacticaseibacillus, and *Turicibacter*; and b. *Bifidobacterium pseudolongum*; and decrease levels of a second organism in the gut microbiome in comparison to a subject not treated with the composition, wherein the second organism is selected from the group consisting of a member of a genus selected from the group consisting of *Hyphomicrobium, Solirubrobacter* and *Steroidobacter*.

7. The method of claim 6, wherein the first organism is the member of the genus selected from the group consisting of Lactiplantibacillus, Lacticaseibacillus, and *Turicibacter*.

8. The method of claim 6, wherein the first organism is *Bifidobacterium pseudolongum*.

9. The method of claim 6, wherein the composition comprises AKBA or the extract of *Boswellia serrata* in combination with a live or lyophilized probiotic bacteria.

10. The method of claim 6, wherein the method further comprises administering a second composition comprising a live or lyophilized probiotic bacteria.

11. The method of claim 6, wherein the composition comprises AKBA or the extract of *Boswellia serrata* in combination with a live or lyophilized probiotic bacteria; and the probiotic bacteria is *Bifidobacterium pseudolongum*.

* * * * *